United States Patent
Kim et al.

(10) Patent No.: US 9,627,627 B2
(45) Date of Patent: Apr. 18, 2017

(54) PHOSPHINE OXIDE-BASED COMPOUND AND ORGANIC LIGHT-EMITTING DEVICE INCLUDING THE SAME

(71) Applicants: Samsung Display Co., Ltd., Yongin, Gyeonggi-Do (KR); Industry-Academic Cooperation Foundation Gyeongsang National University, Jinju, Gyeongnam (KR)

(72) Inventors: Mi-Kyung Kim, Yongin (KR); Kwan-Hee Lee, Yongin (KR); Chang-Woong Chu, Yongin (KR); Yun-Hi Kim, Jinju (KR); Soon-Ki Kwon, Jinju (KR); Seung-Jin Yoo, Jinju (KR)

(73) Assignees: Samsung Display Co., Ltd., Samsung-ro, Giheung-Gu, Yongin-si, Gyeonggi-Do (KR); INDUSTRY-ACADEMIC COOPERATION FOUNDATION GYEONGSANG NATIONAL UNIVERSITY, Jinju, Gyeongnam (KR)

(*) Notice: Subject to any disclaimer, the term of this patent is extended or adjusted under 35 U.S.C. 154(b) by 731 days.

(21) Appl. No.: 14/014,732

(22) Filed: Aug. 30, 2013

(65) Prior Publication Data

US 2014/0077190 A1 Mar. 20, 2014

(30) Foreign Application Priority Data

Sep. 14, 2012 (KR) ........................ 10-2012-0102272

(51) Int. Cl.

| | |
|---|---|
| H01L 51/54 | (2006.01) |
| C07F 9/53 | (2006.01) |
| H01L 51/00 | (2006.01) |
| C07F 9/6506 | (2006.01) |
| C07F 9/6561 | (2006.01) |
| C07F 15/00 | (2006.01) |
| H01L 51/50 | (2006.01) |

(52) U.S. Cl.
CPC ........ *H01L 51/0072* (2013.01); *C07F 9/5325* (2013.01); *C07F 9/6561* (2013.01); *C07F 9/65068* (2013.01); *C07F 15/002* (2013.01); *C07F 15/0026* (2013.01); *C07F 15/0033* (2013.01); *C07F 15/0086* (2013.01); *C07F 15/0093* (2013.01); *H01L 51/5072* (2013.01)

(58) Field of Classification Search
None
See application file for complete search history.

(56) References Cited

U.S. PATENT DOCUMENTS

| | | | |
|---|---|---|---|
| 5,086,156 A | 2/1992 | McGrath et al. | |
| 6,396,209 B1 * | 5/2002 | Kido .................. | H01L 51/5052 313/503 |
| 7,063,903 B2 | 6/2006 | Grushin et al. | |
| 2012/0068168 A1 | 3/2012 | Lee et al. | |
| 2012/0256171 A1* | 10/2012 | Terashima .......... | H01L 51/0067 257/40 |
| 2012/0261651 A1* | 10/2012 | Noto ..................... | C09K 11/06 257/40 |

FOREIGN PATENT DOCUMENTS

| | | | |
|---|---|---|---|
| JP | 2004-095221 | | 3/2004 |
| JP | 2004-204140 | | 7/2004 |
| KR | 1020100112868 A | | 10/2010 |
| WO | WO 2010/107244 | * | 9/2010 |
| WO | WO 2011/021385 | * | 2/2011 |

OTHER PUBLICATIONS

"A New Electron Transporting Material for Effective Hole-Blocking and Improved Charge Balance in Highly Efficient Phosphorescent Organic Light Emitting Diodes" authored by Yoo et al. and published in the Journal of Materials Chemistry C (2013), 1, 2217-2223.*

* cited by examiner

*Primary Examiner* — Marc Zimmer
(74) *Attorney, Agent, or Firm* — Robert E. Bushnell, Esq.

(57) ABSTRACT

A phosphine oxide-based compound represented by Formula 1, and an organic light-emitting device including the phosphine oxide-based compound.

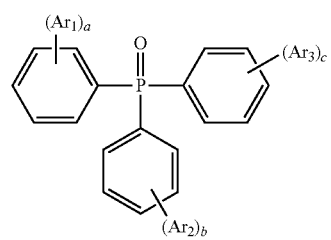

Formula 1 wherein $Ar_1$ through $Ar_3$, and a, b, and c are defined as in the specification.

20 Claims, 5 Drawing Sheets

PHOSPHINE OXIDE-BASED COMPOUND AND ORGANIC LIGHT-EMITTING DEVICE INCLUDING THE SAME

CLAIM OF PRIORITY

This application makes reference to, incorporates the same herein, and claims all benefits accruing under 35 U.S.C. §119 from an application for PHOSPHINE OXIDE-BASED COMPOUND AND ORGANIC LIGHT-EMITTING DEVICE INCLUDING THE SAME earlier filed in the Korean Intellectual Property Office on 14 Sep. 2012 and there duly assigned Serial No. 10-2012-0102272.

BACKGROUND OF THE INVENTION

Field of the Invention

The present invention relates to a phosphine oxide-based compound for organic light-emitting devices, and an organic light-emitting device including the same.

Description of the Related Art

Organic light-emitting devices (OLEDs), which are self-emitting devices, have advantages such as wide viewing angles, excellent contrast, quick response, high brightness, excellent driving voltage characteristics. The OLEDs can provide multicolored images.

A typical OLED has a structure including a substrate, and an anode, a hole transport layer (HTL), an emission layer (EML), an electron transport layer (ETL), and a cathode which are sequentially stacked on the substrate. In this regard, the HTL, the EML, and the ETL are organic thin films formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

SUMMARY OF THE INVENTION

The present invention provides a phosphine oxide-based compound having a novel structure and an organic light-emitting device including the phosphine oxide-based compound.

According to an aspect of the present invention, there is provided a phosphine oxide-based compound represented by Formula 1 below:

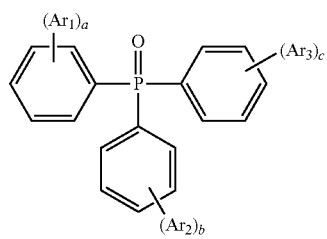

Formula 1 wherein $Ar_1$ to $Ar_3$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or an N-containing electron withdrawing group; a, b and c may be each independently an integer from 1 to 5; and at least one of a number of $Ar_1$s, b number of $Ar_2$s, and c number of $Ar_3$s may be an N-containing electron withdrawing group, wherein the N-containing electron withdrawing group may be selected from among a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl group, a substituted or unsubstituted pyrimidinyl group, a substituted or unsubstituted benzoimidazolyl group, a substituted or unsubstituted indolyl group, a substituted or unsubstituted purinyl group, a substituted or unsubstituted quinolinyl group, a substituted or unsubstituted isoquinolyl group, a substituted or unsubstituted phthalazinyl group, a substituted or unsubstituted indolizinyl group, a substituted or unsubstituted naphthyridinyl group, a substituted or unsubstituted quinazolinyl group, a substituted or unsubstituted cinnolinyl group, a substituted or unsubstituted indazolyl group, a substituted or unsubstituted isothiazolyl group, a substituted or unsubstituted isoxazolyl group, a substituted or unsubstituted triazinyl group, a substituted or unsubstituted oxadiazolyl group, a substituted or unsubstituted pyridazinyl group, a substituted or unsubstituted triazolyl group, a substituted or unsubstituted tetrazolyl group, a substituted or unsubstituted benzothiazolyl group, and a substituted or unsubstituted benzoxazolyl group.

According to another aspect of the present invention, there is provided an organic light-emitting device including a first electrode; a second electrode disposed opposite to the first electrode; and an organic layer disposed between the first electrode and the second electrode and including an emission layer, wherein the organic layer may include at least one of the above-described phosphine oxide-based compounds.

BRIEF DESCRIPTION OF THE DRAWINGS

A more complete appreciation of the present invention, and many of the attendant advantages thereof, will be readily apparent as the present invention becomes better understood by reference to the following detailed description when considered in conjunction with accompanying drawings in which like reference symbols indicate the same or similar components, wherein.

DETAILED DESCRIPTION OF THE INVENTION

Figure 1:
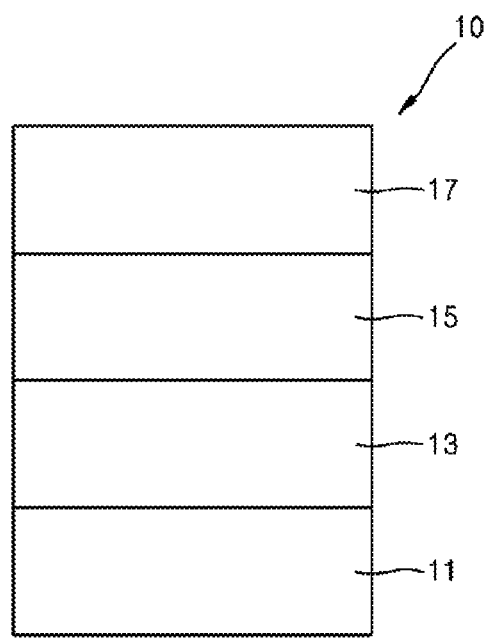
FIG. 1 schematically illustrates a structure of an organic light-emitting device according to an embodiment of the present invention.

Hereinafter, the present invention will become more apparent by describing in detail exemplary embodiments with references to the attached drawings regarding the above features and advantages.

As used herein, the term "and/or" includes any and all combinations of one or more of the associated listed items. Expressions such as "at least one of", when preceding a list of elements, modify the entire list of elements and do not modify the individual elements of the list.

According to an aspect of the present invention, there is provided a phosphine oxide-based compound represented by Formula 1 below:

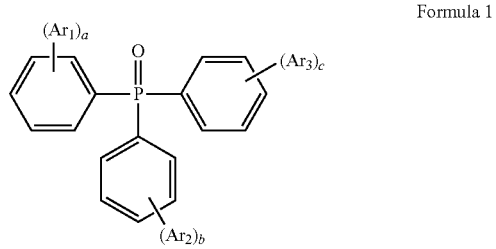

Formula 1

In Formula 1 above, $Ar_1$ to $Ar_3$ may be each independently hydrogen, deuterium, a halogen atom, a hydroxyl group, a cyano group, a nitro group, an amino group, an amidino group, hydrazine, hydrazone, a carboxyl group and a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or an N-containing electron withdrawing group; a, b, and c may be each independently an integer from 1 to 5; at least one of a number of $Ar_1$s, b number of $Ar_2$s, and c number of $Ar_3$s may be an N-containing electron withdrawing group.

The N-containing electron withdrawing group may be a monocyclic heteroaryl group or a bicyclic heteroaryl group with two condensed rings, each group including N as an essential ring member atom.

For example, the N-containing electron withdrawing group may be selected from among a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl group, a substituted or unsubstituted pyrimidinyl group, a substituted or unsubstituted benzoimidazolyl group, a substituted or unsubstituted indolyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted indolizinyl group, a substituted or unsubstituted naphthyridinyl group, a substituted or unsubstituted quinazolinyl group, a substituted or unsubstituted cinnolinyl group, a substituted or unsubstituted indazolyl group, a substituted or unsubstituted isothiazolyl group, a substituted or unsubstituted isoxazolyl group, a substituted or unsubstituted triazinyl group, a substituted or unsubstituted oxadiazolyl group, a substituted or unsubstituted pyridazinyl group, a substituted or unsubstituted triazolyl group, a substituted or unsubstituted tetrazolyl group, a substituted or unsubstituted benzothiazolyl group, and a substituted or unsubstituted benzoxazolyl group.

In some other embodiments, the N-containing electron withdrawing group may be selected from among a substituted or unsubstituted pyridinyl group, a substituted or unsubstituted pyrimidinyl group, a substituted or unsubstituted pyrazinyl group, a substituted or unsubstituted triazinyl group, a substituted or unsubstituted quinolinyl group, a substituted or unsubstituted isoquinolinyl group, a substituted or unsubstituted benzoimidazolyl group, a substituted or unsubstituted imidazopyridinyl group, a substituted or unsubstituted imidazopyrimidinyl group, a substituted or unsubstituted benzothiazolyl group, and a substituted or unsubstituted benzoxazolyl group, but are not limited thereto.

In some other embodiments, the N-containing electron withdrawing group may be selected from among groups represented by Formulae 2A to 2M:

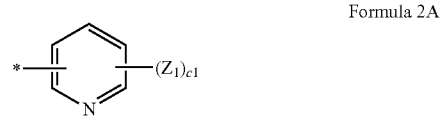

Formula 2A

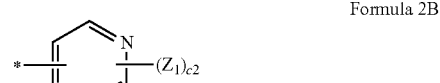

Formula 2B

Formula 2C

Formula 2D

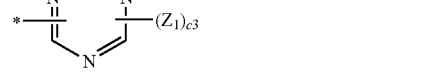

Formula 2E

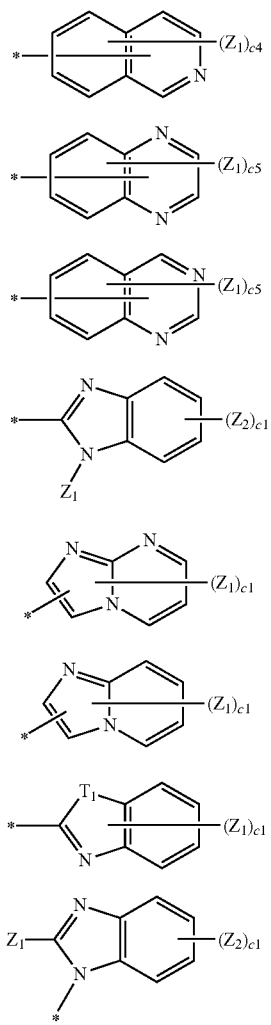

In Formulae 2A to 2M above, $Z_1$ and $Z_2$ may be each independently selected from hydrogen, deuterium, a halogen atom, a hydroxyl group, a cyano group, a nitro group, an amino group, an amidino group, hydrazine, hydrazone, a carboxyl group and a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group and a $C_6$-$C_{60}$ aryl group; a $C_6$-$C_{60}$ aryl group substituted with at least one of —F, —CN, and a $C_1$-$C_{10}$ alkyl group; and a $C_6$-$C_{60}$ aryloxy group, a $C_6$-$C_{60}$ arylthio group and a $C_2$-$C_{60}$ heteroaryl group; $c_1$ may be an integer from 1 to 4; $c_2$ may be an integer from 1 to 3; $c_3$ may be an integer from 1 to 2; $c_4$ may be an integer from 1 to 6; and $c_5$ may be an integer from 1 to 5; and $T_1$ may be O or S.

In some embodiments, in Formulae 2A to 2M, $Z_1$ and $Z_2$ may be each independently hydrogen, deuterium, a halogen atom, a hydroxyl group, a cyano group, a nitro group, an amino group, an amidino group, hydrazine, hydrazone, a carboxylic group or a salt thereof, a sulfonic acid group or a phosphoric acid group or a salt thereof, a $C_1$-$C_{20}$ alkyl group, a $C_1$-$C_{20}$ alkoxy group, a phenyl group, a naphthyl group, an anthryl group, or a phenanthrenyl group, but are not limited thereto.

In some embodiments, the N-containing electron withdrawing group may be a group represented by Formula 2I above (wherein $Z_1$ is a phenyl group, a naphthyl group, an anthryl group, or a phenanthrenyl group), but is not limited thereto.

In Formula 1 above, a indicates the number of $Ar_1$s, b indicates the number of $Ar_2$s, and c indicates the number of $Ar_3$s. If a in Formula 1 is at least two, at least two $Ar_1$ may be the same or different. If b is at least two, at least two $Ar_2$ may be the same or different. If c is at least two, at least two $Ar_3$ may be the same or different.

In Formula 1 above, at least two of the a number of $Ar_1$s, the b number of $Ar_2$s, and the c number of $Ar_3$s may be N-containing electron withdrawing groups.

In some embodiments, in Formula 1 above, a, b, and c may be all 1, wherein at least one of $Ar_1$ to $Ar_3$, or at least two thereof, may be an N-containing electron withdrawing group, but is not limited thereto.

In Formula 1 above, $Ar_1$ to $Ar_3$ may be each independently hydrogen, deuterium, a halogen atom, a hydroxyl group, a cyano group, a nitro group, an amino group, an amidino group, hydrazine, hydrazone, a carboxyl group and a salt thereof, a sulfonic acid group or a salt thereof, a phosphoric acid group or a salt thereof, a $C_1$-$C_{20}$ alkyl group (for example, a $C_1$-$C_{10}$ alkyl group), a $C_1$-$C_{20}$ alkoxy group (for example, a $C_1$-$C_{10}$ alkoxy group), a phenyl group, a naphthyl group, an anthryl group, a phenanthrenyl group, or an N-containing electron withdrawing group; a, b, and c may be each independently 1, 2, or 3, wherein at least one of the a number of $Ar_1$, the b number of $Ar_2$, and the c number of $Ar_3$ (for example, at least two of the a number of $Ar_1$, the b number of $Ar_2$, and the c number of $Ar_3$) may be an N-containing electron withdrawing group. In this regard, the "N-containing electron withdrawing group" is as defined above.

In some embodiments, the phosphine oxide-based compound may be a compound represented by Formula 1A below:

Formula 1A

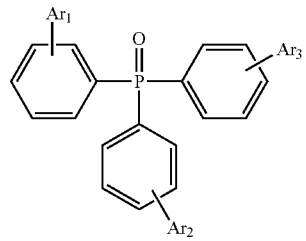

In Formula 1A, $Ar_1$, $Ar_2$, and $Ar_3$ may be as defined above.

In some embodiments, in Formula 1A, $Ar_1$ to $Ar_3$ may be each independently hydrogen, deuterium, a halogen atom, a hydroxyl group, a cyano group, a nitro group, an amino group, an amidino group, hydrazine, hydrazone, a carboxyl group and a salt thereof, a sulfonic acid group or a salt thereof, a phosphoric acid group or a salt thereof, a $C_1$-$C_{20}$ alkyl group (for example, a $C_1$-$C_{10}$ alkyl group), a $C_1$-$C_{20}$ alkoxy group (for example, a $C_1$-$C_{10}$ alkoxy group), a phenyl group, a naphthyl group, an anthryl group, a phenanthrenyl group, or an N-containing electron withdrawing group, wherein at least one of $Ar_1$, $Ar_2$, and $Ar_3$ (for example, at least two thereof) may be an N-containing electron withdrawing group; and the N-containing electron withdrawing group may be selected from among the groups represented by Formulae 2A to 2M above, but are not limited thereto. The above descriptions of Formulae 2A to 2M are referred to herein.

In some embodiments, the phosphine oxide-based compound may be a compound represented by Formula 1A-(1) below:

Formula 1A-(1)

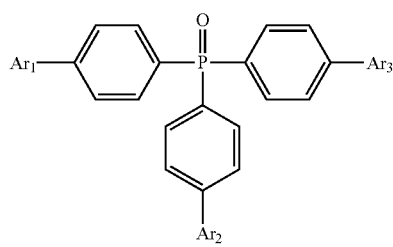

In Formula 1A-(1), $Ar_1$, $Ar_2$, and $Ar_3$ may be as defined above.

For example, in Formula 1A-(1), $Ar_1$ to $Ar_3$ may be each independently hydrogen, deuterium, a halogen atom, a hydroxyl group, a cyano group, a nitro group, an amino group, an amidino group, hydrazine, hydrazone, a carboxyl group and a salt thereof, a sulfonic acid group or a salt thereof, a phosphoric acid group or a salt thereof, a $C_1$-$C_{20}$ alkyl group (for example, a $C_1$-$C_{10}$ alkyl group), a $C_1$-$C_{20}$ alkoxy group (for example, a $C_1$-$C_{10}$ alkoxy group), a phenyl group, a naphthyl group, an anthryl group, a phenanthrenyl group, or an N-containing electron withdrawing group, wherein at least one of $Ar_1$, $Ar_2$ and $Ar_3$ (for example, at least two thereof) may be an N-containing electron withdrawing group; and the N-containing electron withdrawing group may be selected from among groups represented by Formulae 2A to 2M, but are not limited thereto. The above descriptions of Formulae 2A to 2M are referred to herein. In some embodiments, in Formulae 2A to 2M, $Z_1$ and $Z_2$ may be each independently hydrogen, deuterium, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, or a phenanthrenyl group; $c_1$ may be an integer from 1 to 4; $c_2$ may be an integer from 1 to 3; $c_3$ may be an integer from 1 to 2; $c_4$ may be an integer from 1 to 6; $c_5$ may be an integer from 1 to 5; and $T_1$ may be O or S, but are not limited thereto.

In some embodiments, the phosphine oxide-based compound may be one of Compounds 1 to 6 below, but is not limited thereto:

Compound 1

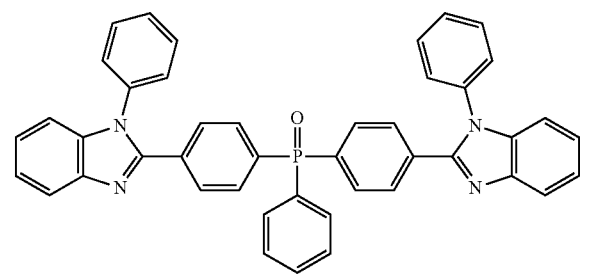

Compound 2

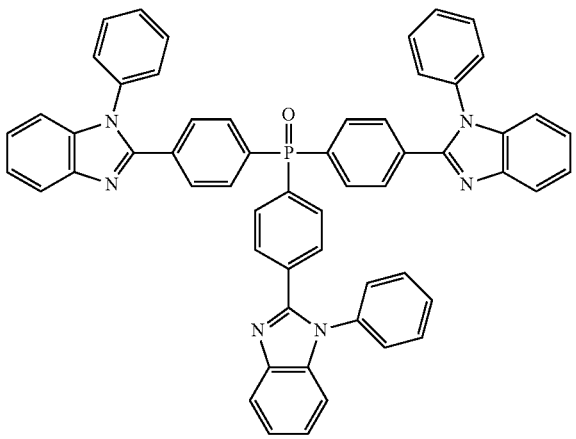

Compound 3

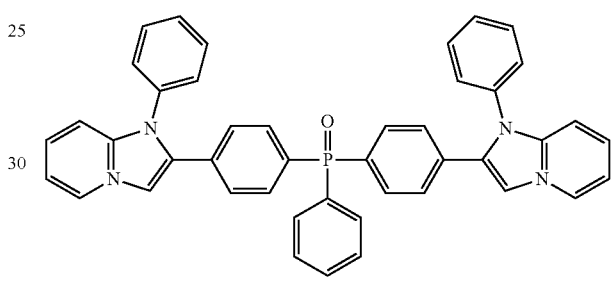

Compound 4

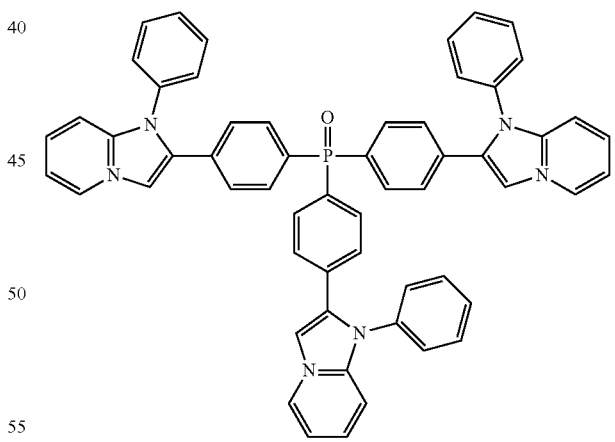

Compound 5

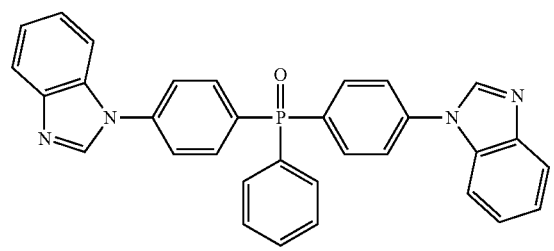

Compound 6

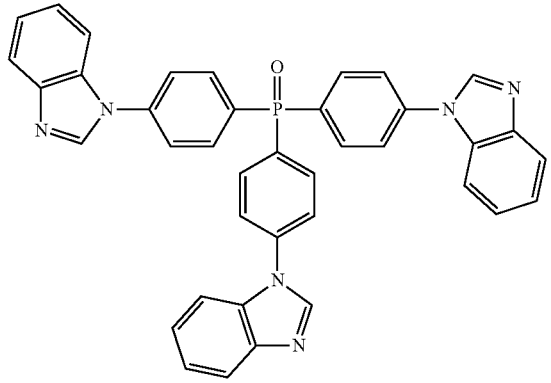

Examples of the unsubstituted $C_1$-$C_{60}$ alkyl group used herein may be linear or branched $C_1$-$C_{60}$ alkyl groups, such as methyl group, ethyl group, propyl group, isobutyl group, sec-butyl group, pentyl group, iso-amyl group, hexyl group, or the like. In the substituted $C_1$-$C_{60}$ alkyl group, at least one hydrogen of the unsubstituted $C_1$-$C_{60}$ alkyl group described above may be substituted with deuterium, a halogen atom, a hydroxyl group, a nitro group, a cyano group, an amino group, an amidino group, hydrazine, hydrazone, a carboxyl group or salts thereof, a sulfonic acid group or salts thereof, a phosphoric acid group or salts thereof, a $C_1$-$C_{60}$ alkyl group, a $C_2$-$C_{60}$ alkenyl group, a $C_2$-$C_{60}$ alkynyl group, a $C_6$-$C_{60}$ aryl group, a $C_2$-$C_{60}$ heteroaryl group, —N($Q_{11}$)($Q_{12}$), or —Si($Q_{13}$)($Q_{14}$)($Q_{15}$), wherein $Q_1$ to $Q_{15}$ may be each independently selected from the group consisting of hydrogen, a $C_1$-$C_{60}$ alkyl group, a $C_2$-$C_{60}$ alkenyl group, a $C_2$-$C_{60}$ alkynyl group, a $C_5$-$C_{60}$ aryl group, and a $C_2$-$C_{60}$ heteroaryl group.

The unsubstituted $C_1$-$C_{60}$ alkoxy group may be a group represented by —OA, wherein A may be an unsubstituted $C_1$-$C_{60}$ alkyl group described above. Examples of the unsubstituted $C_1$-$C_{60}$ alkoxy group may be a methoxy group, an ethoxy group, and an isopropyloxy group. At least one hydrogen in the unsubstituted $C_1$-$C_{60}$ alkoxy group may be substituted with those substituents described above in conjunction with the substituted $C_1$-$C_{60}$ alkyl group.

As used herein, the unsubstituted $C_2$-$C_{60}$ alkenyl group may be a hydrocarbon chain having a carbon-carbon double bond in the center or at a terminal of the unsubstituted $C_2$-$C_{60}$ alkyl group. Examples of the unsubstituted $C_2$-$C_{60}$ alkenyl group may be an ethenyl group, a propenyl group, a butenyl group, and the like. At least one hydrogen in the unsubstituted $C_2$-$C_{60}$ alkenyl group may be substituted with those substituents described above in conjunction with the substituted $C_1$-$C_{60}$ alkyl group.

The unsubstituted $C_2$-$C_{60}$ alkynyl group may be a $C_2$-$C_{60}$ alkyl group having at least one carbon-carbon triple bond in the center or at a terminal thereof. Examples of the unsubstituted $C_2$-$C_{60}$ alkynyl group may be an ethenyl group, a propynyl group, and the like. At least one hydrogens in the unsubstituted $C_2$-$C_{60}$ alkynyl group may be substituted with those substituents described above in conjunction with the substituted $C_1$-$C_{60}$ alkyl group.

The unsubstituted $C_6$-$C_{60}$ aryl group may be a monovalent group having a carbocyclic aromatic system having 6 to 60 carbon atoms including at least one aromatic ring. The unsubstituted $C_6$-$C_{60}$ arylene group may be a divalent group having a carbocyclic aromatic system having 6 to 60 carbon atoms including at least one aromatic ring. When the aryl group and the arylene group have at least two rings, they may be fused to each other via a single bond. At least one hydrogen in the unsubstituted $C_6$-$C_{60}$ aryl group and the unsubstituted $C_6$-$C_{60}$ arylene group may be substituted with those substituents described above in conjunction with the $C_1$-$C_{60}$ alkyl group.

Examples of the substituted or unsubstituted $C_6$-$C_{60}$ aryl group may be a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., an o-, m- or p-fluorophenyl group and a dichlorophenyl group), a dicyanophenyl group, a trifluoromethoxyphenyl group, an o-, m- or p-tolyl group, an o-, m- or p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, hexacenyl group, a rubicenyl group, a coronenyl group, a trinaphthylenyl group, a heptaphenyl group, a heptacenyl group, a pyranthrenyl group, and an ovalenyl group. Examples of the substituted $C_6$-$C_{60}$ aryl group may be inferred based on those of the unsubstituted $C_6$-$C_{60}$ aryl group and the substituted $C_1$-$C_{30}$ alkyl group described above. Examples of the substituted or unsubstituted $C_6$-$C_{60}$ arylene group may be inferred based on those examples of the substituted or unsubstituted $C_6$-$C_{60}$ aryl group described above.

The unsubstituted $C_2$-$C_{60}$ heteroaryl group may be a monovalent group having at least one aromatic ring having at least one of the heteroatoms selected from the group consisting of N, O, P, and S. The unsubstituted $C_2$-$C_{60}$ heteroarylene group may be a divalent group having at least one aromatic ring having at least one of the heteroatoms selected from the group consisting of N, O, P, and S. In this regard, when the $C_2$-$C_{60}$ heteroaryl group and the $C_2$-$C_{60}$ heteroarylene group have at least two rings, they may be fused to each other via a single bond. At least one hydrogen in the $C_2$-$C_{60}$ heteroaryl group and the $C_2$-$C_{60}$ heteroarylene group may be substituted with those substituents described with reference to the $C_1$-$C_{60}$ alkyl group.

The substituted or unsubstituted $C_6$-$C_{60}$ aryloxy group indicates —$OA_2$ (where $A_2$ is a substituted or unsubstituted $C_6$-$C_{60}$ aryl group described above). The substituted or unsubstituted $C_6$-$C_{60}$ arylthio group indicates —$SA_3$ (where $A_3$ is a substituted or unsubstituted $C_6$-$C_{60}$ aryl group described above).

The examples of the unsubstituted $C_3$-$C_{10}$ cycloalkyl group include a cyclopentyl and a cyclohexyl and the examples of the unsubstituted $C_3$-$C_{10}$ cycloalkenyl group include a cyclopentenyl and a cyclohexenyl. At least one hydrogen in the unsubstituted $C_3$-$C_{10}$ cycloalkyl group and the unsubstituted $C_3$-$C_{10}$ cycloalkenyl group may be substituted with those substituents described with reference to the $C_1$-$C_{60}$ alkyl group.

Since the phosphine oxide-based compound of Formula 1 above includes at least one of the N-containing electron withdrawing group having a small molecular size described above, the phosphine oxide-based compound of Formula 1 may have high electron mobility. Therefore, an organic light-emitting device including the phosphine oxide-based compound represented by Formula 1 above may have a low driving voltage and a high efficiency.

The phosphine oxide-based compound of Formula 1 includes a "benzen" as an aromatic ring directly linked to "P", and thus may have a relatively small molecular weight, and thus a high sublimation purification yield. Furthermore, due to the "benzen" as an aromatic ring directly linked to "P", the phosphine oxide-based compound of Formula 1 may have a high electron density between the phosphine oxide core and the N-containing electron withdrawing group, and thus the "benzen" may not be involved in molecular resonance. Therefore, the "benzen" of the phosphine oxide-based compound of Formula 1 may only provide a steric effect to molecules but suppress molecular interactions. Accordingly, the phosphine oxide-based compound of Formula 1 may have good electron transporting characteristics. With the assumption of a virtual compound having the same structure as Formula 1 except for including a "naphthalene" as an aromatic ring directly linked to "P", the virtual compound may have a high electron density in the "naphthalene", which is involved in molecular resonance, so that LUMO electrons may not be uniformly distributed in the N-containing electron withdrawing group, and the virtual compound may have significantly lower electron transporting characteristics.

The phosphine oxide-based compound of Formula 1 has a low HOMO energy level (i.e., with a large absolute of the HOMO energy level), and thus may effectively prevent holes injected via the first electrode (anode) from passing through the emission layer. For example, the phosphine oxide-based compound of Formula 1 may have a highest occupied molecular orbital (HOMO) energy level of about −7.0 eV or less, but is not limited thereto.

The phosphine oxide-based compound may be synthesized by using a known organic synthesis method. A synthesis method of the phosphine oxide-based compound may be understood by those of ordinary skill in the art based on the examples that will be described below.

Therefore, an organic light-emitting device including the phosphine oxide-based compound of Formula 1 above may have a low driving voltage, a high efficiency, a high luminance, and a long lifetime.

According to another aspect of the present invention, an organic light-emitting device may include a first electrode, a second electrode disposed opposite to the first electrode, and an organic layer disposed between the first electrode and the second electrode and comprising an emission layer, wherein the organic layer may include at least one of the phosphine oxide-based compounds of Formula 1 described above.

As used herein, for example, the organic layer including at least one phosphine oxide-based compounds means that the organic layer including one of the phosphine oxide-based compounds of Formula 1 above, or at least two different phosphine oxide-based compounds of Formula 1 above.

In some embodiments, the organic layer may include only Compound 1 above as the phosphine oxide-based compound. In this regard, the Compound 1 may be present in the electron transport layer of the organic light-emitting device.

In some embodiments, the organic layer may include Compounds 1 and 2 as phosphine oxide-based materials. In this regard, the Compounds 1 and 2 may be present in the same layer (for example, in the electron transport layer) or may be present in different layers (for example, in the hole blocking layer and the electron transport layer, respectively).

The term "organic layer" as used herein refers to a single layer and/or a plurality of layers disposed between the first and second electrodes of the organic light-emitting device.

The organic layer may include at least one layer selected from among a hole injection layer, a hole transport layer, a functional layer having both hole injection and hole transport capabilities (hereinafter, "H-functional layer"), a buffer layer, an electron blocking layer, an emission layer, a hole blocking layer, an electron transport layer, an electron injection layer, and a functional layer having both electron injection and electron transport capabilities (hereinafter, "E-functional layer").

In some embodiments, the organic light-emitting device may further include at least one of a hole injection layer, a hole transport layer, a functional layer having both hole injection and hole transport capabilities, a buffer layer, and an electron blocking layer between the first electrode and the emission layer. In some other embodiments, the organic light-emitting device may further include at least one of a hole blocking layer, an electron transport layer, and a functional layer having both electron injection and electron transport capabilities and an electron injection layer between the emission layer and the second electrode.

In still other embodiments, the organic light-emitting device may further include an electron transport layer between the emission layer and the second electrode, wherein the phosphine oxide-based compound may be included in the electron transport layer. The electron transport layer further comprises a lithium (Li) complex. In yet other embodiments, the organic light-emitting devices may further include a hole blocking layer and an electron transport layer between the emission layer and the second electrode, wherein the phosphine oxide-based compound may be included in the hole blocking layer, but is not limited thereto.

The emission layer of the light-emitting device may include a host and a dopant, and the dopant may be a phosphorescent dopant emitting light based on the mechanism of phosphorescence. In some embodiments, the phosphorescent dopant may be an organic metal compound including at least one element of iridium (Ir), platinum (Pt), osmium (Os), titanium (Ti), zirconium (Zr), hafnium (Hf), europium (Eu), terbium (Tb) and thulium (Tm).

FIG. 1 is a schematic sectional view of an organic light-emitting device 10 according to an embodiment of the present invention. Hereinafter, a structure of an organic light-emitting device according to an embodiment of the present invention and a method of manufacturing the same will now be described with reference to FIG. 1.

A substrate 11 may be any substrate that is used in existing organic light-emitting devices. In some embodiments the substrate 11 may be a glass substrate or a transparent plastic substrate with strong mechanical strength, thermal stability, transparency, surface smoothness, ease of handling, and water resistance.

A first electrode 13 may be formed by depositing or sputtering a first electrode-forming material onto a surface of the substrate 11. When the first electrode 13 is an anode, a material having a high work function may be used as the first electrode-forming material to facilitate hole injection.

The first electrode 13 may be a reflective electrode or a transmission electrode. Transparent and conductive materials such as ITO, IZO, SnO$_2$, and ZnO may be used to form the first electrode 13. The first electrode 13 may be formed as a reflective electrode using magnesium (Mg), aluminum (Al group, aluminum-lithium (Al—Li), calcium (Ca), magnesium-indium (Mg—In), magnesium-silver (Mg—Ag), or the like.

The first electrode 13 may have a single-layer structure or a multi-layer structure including at least two layers. For example, the first electrode 13 may have a three-layered structure of ITO/Ag/ITO, but is not limited thereto.

The organic layer 15 may be disposed on the first electrode 13.

The organic layer 15 may include a hole injection layer (HIL GROUP), a hole transport layer (HTL GROUP), a buffer layer, an emission layer (EML GROUP), an electron transport layer (ETL GROUP), and an electron injection layer (EIL GROUP).

The HIL may be formed on the first electrode 13 by vacuum deposition, spin coating, casting, Langmuir-Blodgett (LB) deposition, or the like.

When the HIL is formed using vacuum deposition, vacuum deposition conditions may vary according to a compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 Å/sec to about 100 Å/sec. However, the deposition conditions are not limited thereto.

When the HIL is formed using spin coating, the coating conditions may vary according to a compound that is used to form the HIL, and the desired structure and thermal properties of the HIL to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto.

The HIL may be formed of any material that is commonly used to form a HIL. Non-limiting examples of the material that may be used to form the HIL may be N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4''-tris(3-methylphenylphenylamino)triphenylamine (m-MTDATA), N,N'-di(1-naphthyl group-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrene-sulfonate) (PEDOT/PSS), polyaniline/camphor sulfonic acid (Pani/CSA), and polyaniline)/poly(4-styrenesulfonate (PANI/PSS).

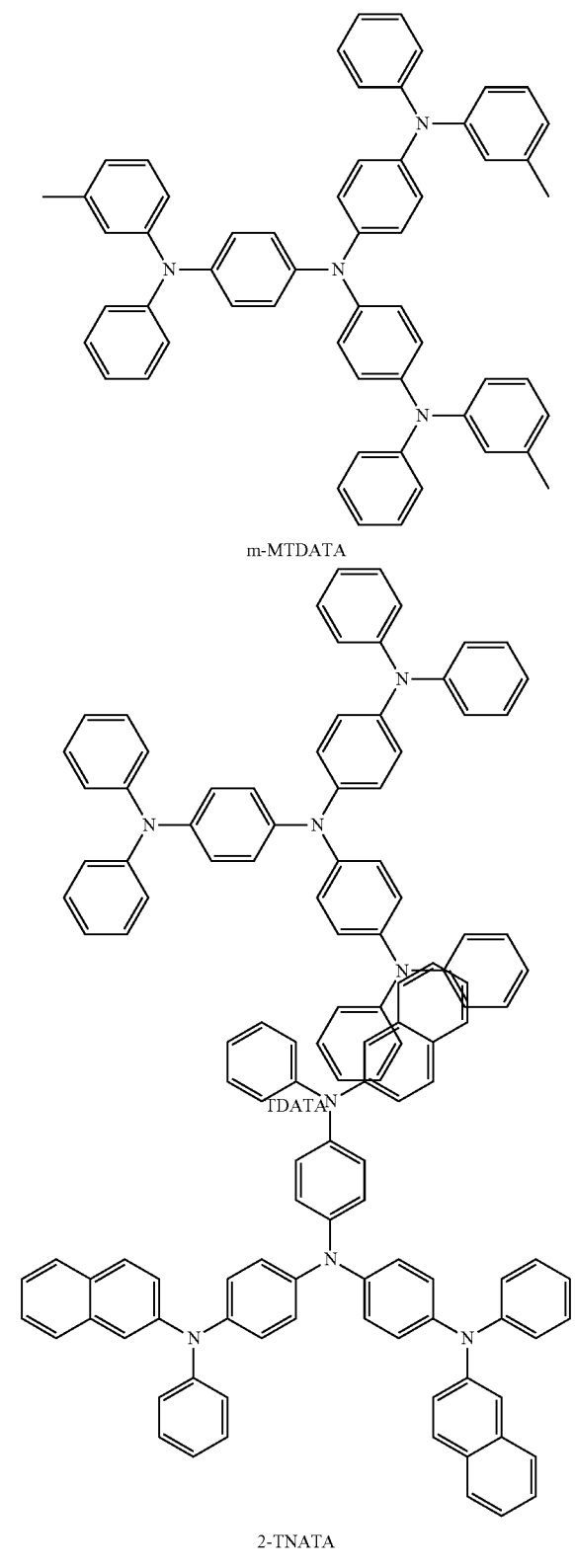

m-MTDATA

TDATA

2-TNATA

The thickness of the HIL may be about 100 Å to about 10000 Å, and in some embodiments, may be from about 100 Å to about 1000 Å. When the thickness of the HIL is within these ranges, the HIL may have good hole injecting ability without a substantial increase in driving voltage.

Then, a HTL may be formed on the HIL by using vacuum deposition, spin coating, casting, Langmuir-Blodgett (LB) deposition, or the like. When the HTL is formed using vacuum deposition or spin coating, the conditions for deposition and coating may be similar to those for the formation of the HIL, though the conditions for the deposition and coating may vary according to a material that is used to form the HTL.

Non-limiting examples of suitable known HTL forming materials may be carbazole derivatives, such as N-phenyl-carbazole or polyvinylcarbazole, N,N'-bis(3-methylphenyl group-N,N'-diphenyl-[1,1-biphenyl]-4,4'-diamine (TPD), 4,4',4''-tris(N-carbazolyl grouptriphenylamine (TCTA), and N,N'-di(1-naphthyl group-N,N'-diphenylbenzidine) (NPB).

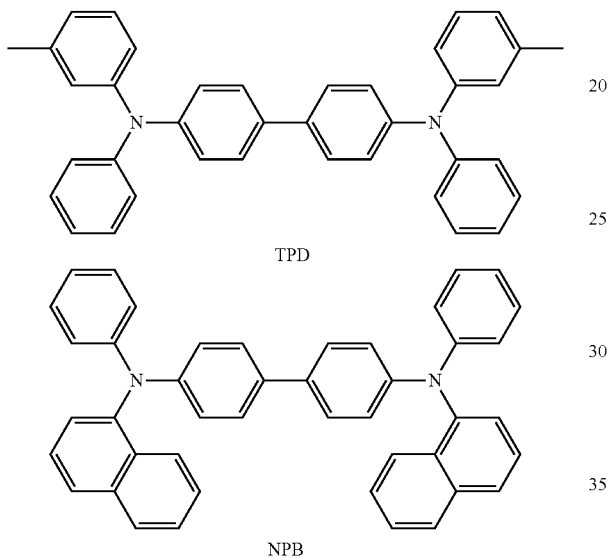

The thickness of the HTL may be from about 50 Å to about 2000 Å, and in some embodiments, may be from about 100 Å to about 1500 Å. When the thickness of the HTL is within these ranges, the HTL may have good hole transporting ability without a substantial increase in driving voltage.

At least some of the hole transport layer materials may be used as materials for the electron blocking layer. The electron blocking layer may prevent the electrons injected via the second electrode (cathode) from migrating toward the first electrode (anode) through the emission layer. For example, TCTA may have both hole transporting and electron blocking capabilities.

The H-functional layer (having both hole injection and hole transport capabilities) may contain at least one material from each group of the hole injection layer materials and hole transport layer materials. The thickness of the H-functional layer may be from about 500 Å to about 10,000 Å, and in some embodiments, may be from about 100 Å to about 1,000 Å. When the thickness of the H-functional layer is within these ranges, the H-functional layer may have good hole injection and transport capabilities without a substantial increase in driving voltage.

In some embodiments, at least one of the HIL, HTL, and H-functional layer may include at least one of a compound of Formula 300 below and a compound of Formula 301 below:

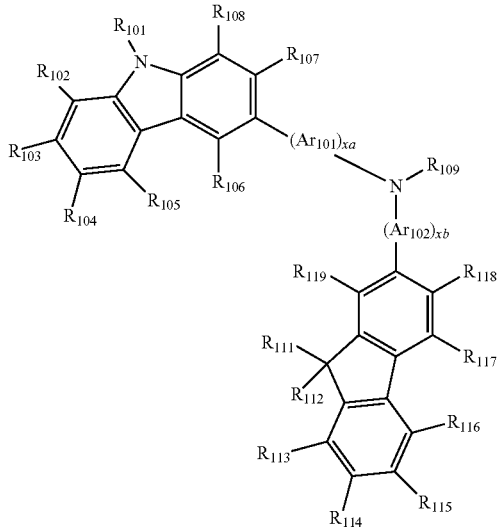

Formula 300

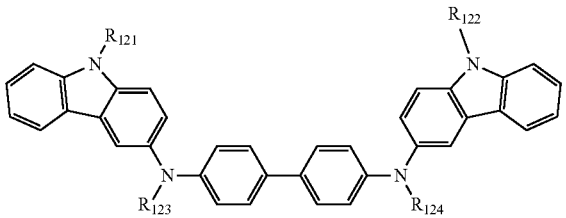

Formula 301

In Formula 300, $Ar_{101}$ and $Ar_{102}$ may be each independently a substituted or unsubstituted $C_6$-$C_{60}$ arylene group. In some embodiments, $Ar_{101}$ and $Ar_{102}$ may be each independently one of a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylenylene group, a chrysenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylenylene group, a chrysenylene group, a naphthacenylene group, a picenylene group, a perylenylene group, and a pentacenylene group that are substituted with at least one of deuterium, a halogen atom, a hydroxyl group, a nitro group, a cyano group, an amino group, an amidino group, hydrazine, hydrazone, a carboxyl group or salt thereof, a sulfuric acid group or salt thereof, a phosphoric acid group or salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group.

In Formula 300, xa and xb may be each independently an integer from 0 to 5, for example, may be 0, 1, or 2. For example, xa may be 1, and xb may be 0, but are not limited thereto.

In Formulae 300 and 301 above, $R_{101}$ to $R_{108}$, $R_{111}$ to $R_{119}$, and $R_{121}$ to $R_{124}$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. In some embodiments, $R_{101}$ to $R_{108}$, $R_{111}$ to $R_{119}$, and $R_{121}$ to $R_{124}$ may be each independently one of hydrogen; deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group and a $C_1$-$C_{10}$ alkoxy group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, and a phosphoric acid group or a salt thereof; a phenyl group; a naphthyl group; an anthryl group; a fluorenyl group; a pyrenyl group; and a phenyl group, a naphthyl group, an anthryl group, a fluorenyl group, and a pyrenyl group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group.

In Formula 300, $R_{109}$ may be one of a phenyl group, a naphthyl group, an anthryl group, a biphenyl group, a pyridyl group; and a phenyl group, a naphthyl group, an anthryl group, a biphenyl group, and a pyridyl group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

In an embodiment the compound of Formula 300 may be a compound represented by Formula 300A below:

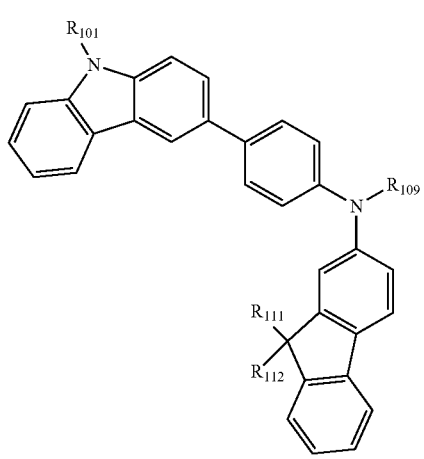

Formula 300A

In Formula 300A, $R_{101}$, $R_{111}$, $R_{112}$, and $R_{109}$ may be as defined above.

In some non-limiting embodiments, at least one of the HIL, HTL, and H-functional layer may include at least one of compounds 301 to 320 below:

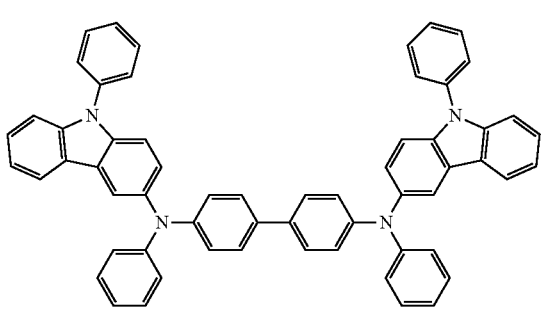

301

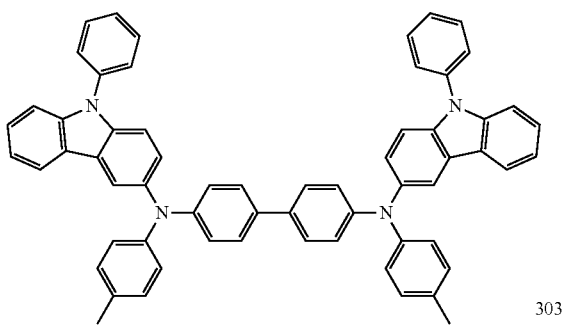

302

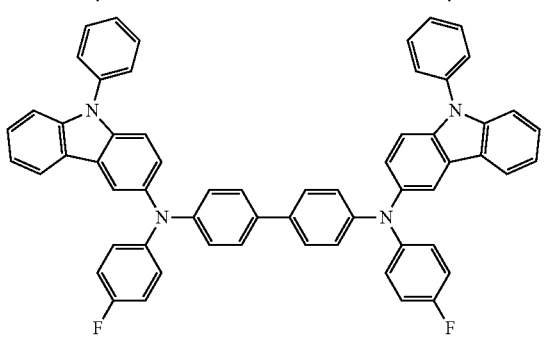

303

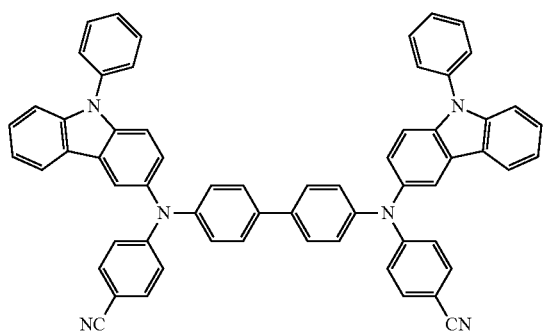
304
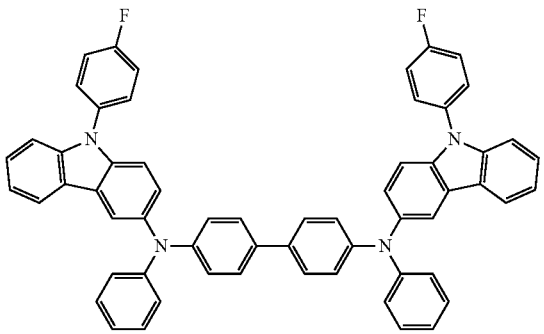
308
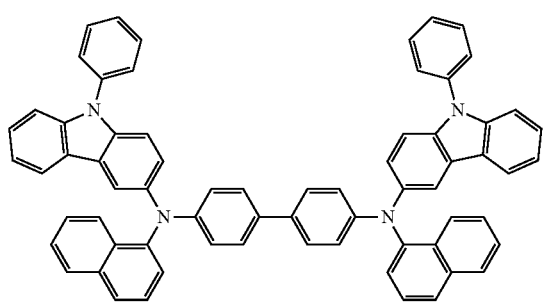
305
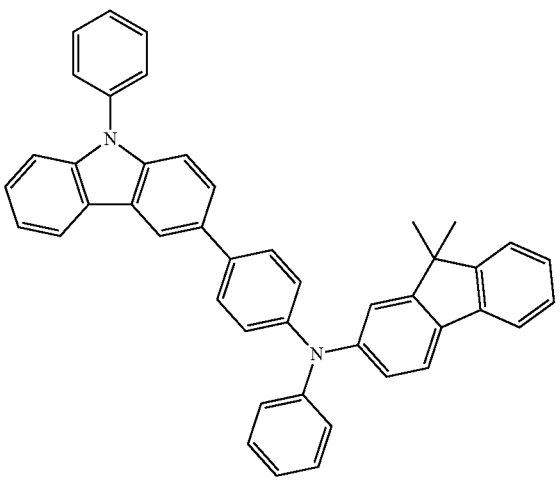
309
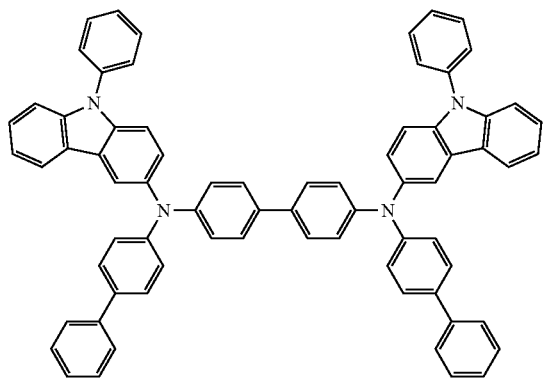
306
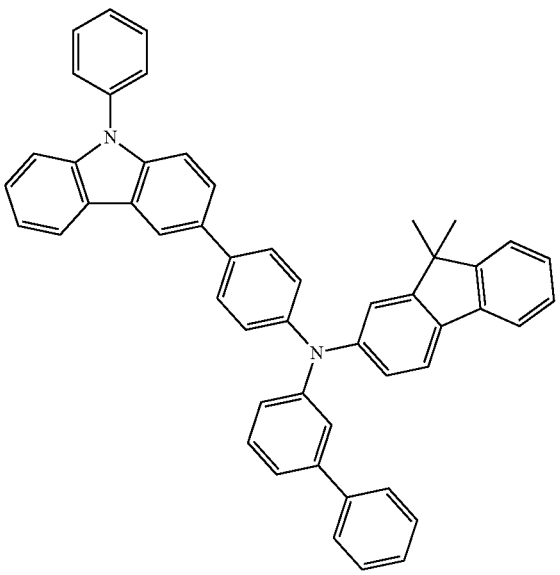
310
307

21
-continued
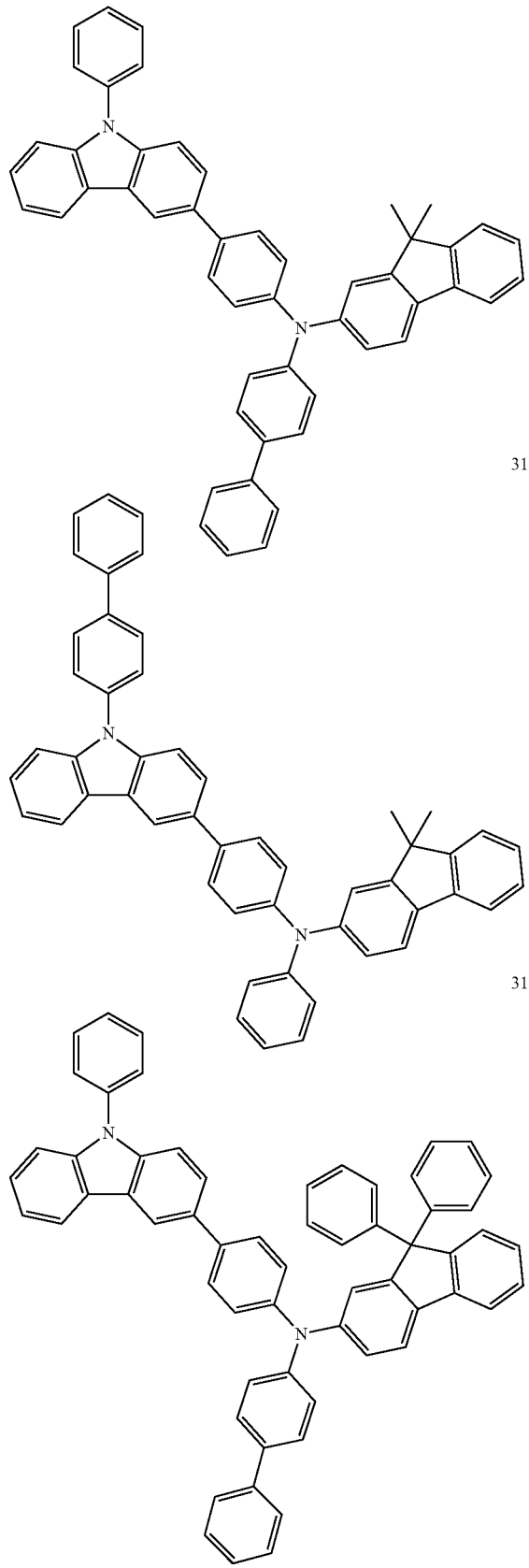
22
-continued
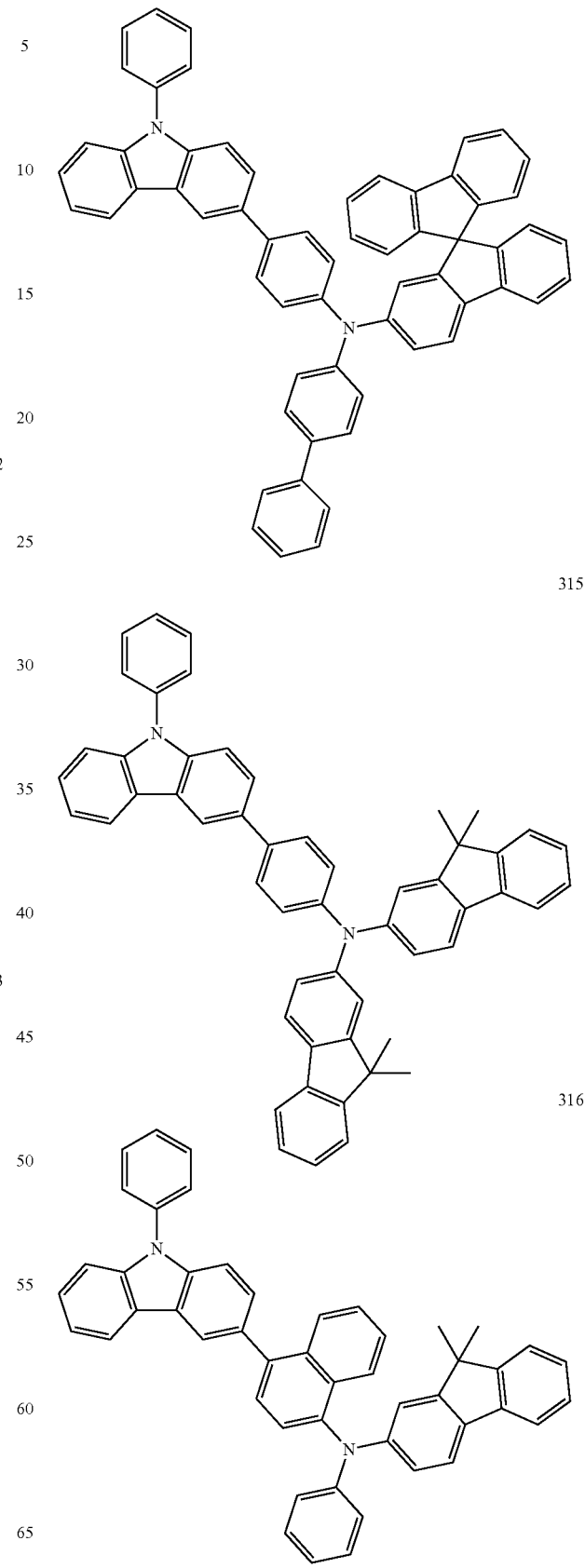

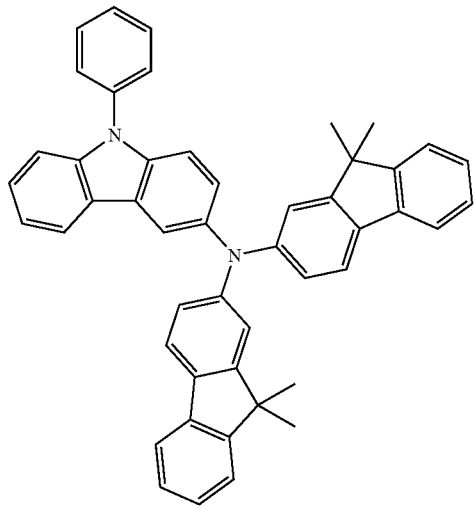

317

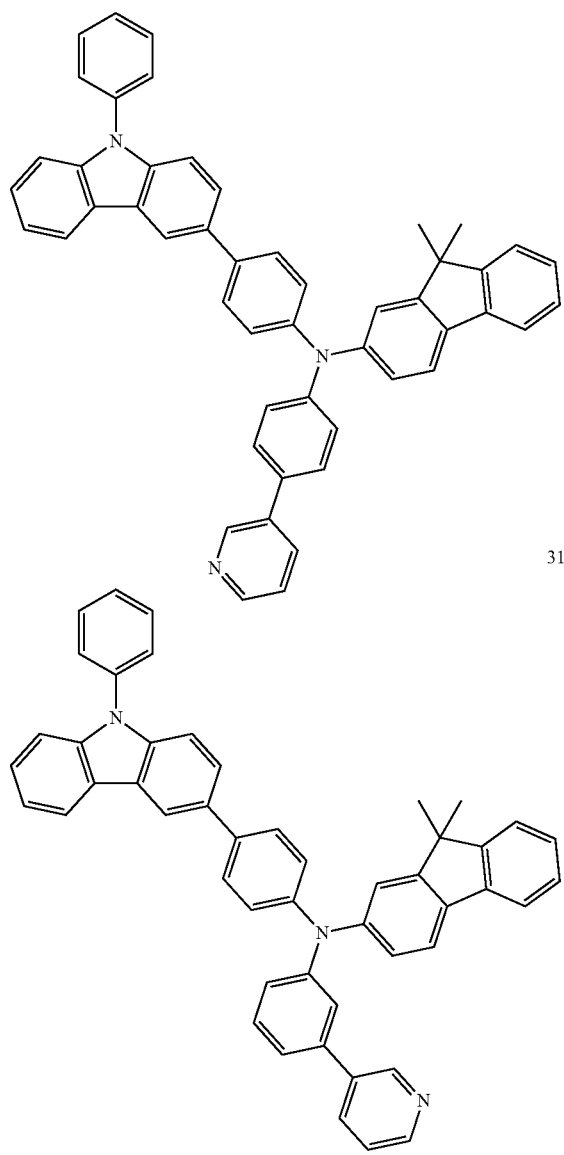

318

319

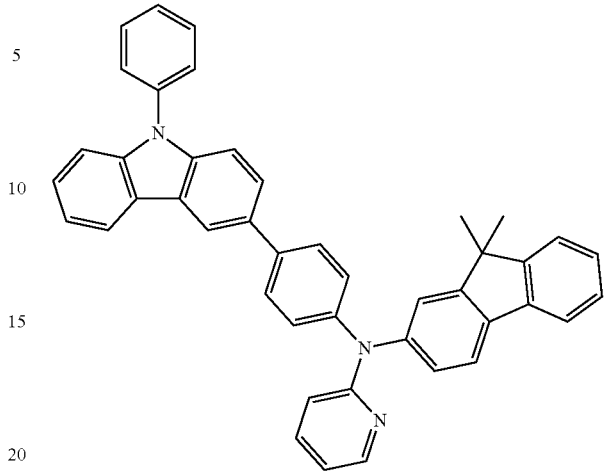

320

At least one of the HIL, HTL, and H-functional layer may further include a charge-generating material for improved layer conductivity, in addition to a known hole injecting material, hole transport material, and/or material having both hole injection and hole transport capabilities as described above.

The charge-generating material may be, for example, a p-dopant. The p-dopant may be one of quinine derivatives, metal oxides, and compounds with a cyano group, but are not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as Compound 200 below.

Compound 200

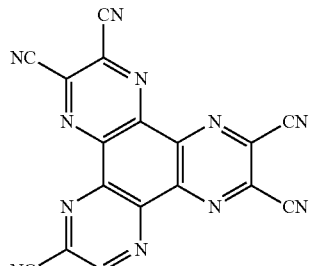

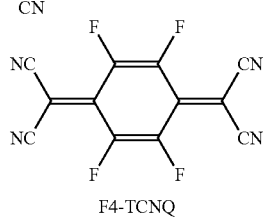

F4-TCNQ

When the hole injection layer, hole transport layer, or H-functional layer further includes a charge-generating material, the charge-generating material may be homogeneously dispersed or inhomogeneously distributed in the layer.

A buffer layer may be disposed between at least one of the HIL, HTL, and H-functional layer, and the EML. The buffer layer may compensate for an optical resonance distance of light according to a wavelength of the light emitted from the EML, and thus may increase efficiency. The buffer layer may include any hole injecting material or hole transporting material that are widely known. In some other embodiments, the buffer layer may include the same material as one of the materials included in the HIL, HTL, and H-functional layer that underly the buffer layer.

Then, an EML may be formed on the HTL, the H-functional layer, or the buffer layer by vacuum deposition, spin coating, casting, Langmuir-Blodget (LB) deposition, or the like. When the EML is formed using vacuum deposition or spin coating, the deposition and coating conditions may be similar to those for the formation of the HIL, though the conditions for deposition and coating may vary according to the material that is used to form the EML.

The emission layer may include at least one of the phosphine oxide-based compounds of Formula 1.

The emission layer may include a host, and a dopant.

Examples of the host may include, but are not limited to, Tris(8-hydroxyquinolinato)aluminium (Alq3), 4,4'-N,N'-dicabazole-biphenyl (CBP), poly(n-vinylcabazole) (PVK), 9,10-di(naphthalene-2-yl)anthracene (ADN), 4,4',4"-tris(N-carbazolyl)-triphenylamine (TCTA), 1,3,5-tris(N-phenyl-benzimidazole-2-yl)benzene (TPBI), 3-tert-butyl-9,10-di(naphth-2-yl)anthracene (TBADN), E3, and distyrylarylene (DSA), dmCBP (refer to Formula below), and Compounds 501 through 509 below.

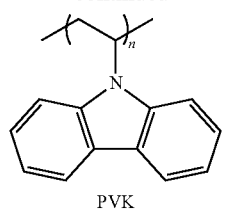

PVK

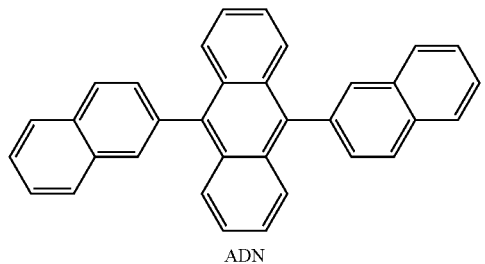

ADN

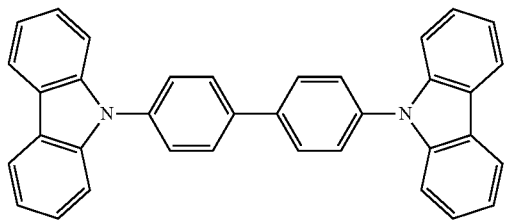

CBP

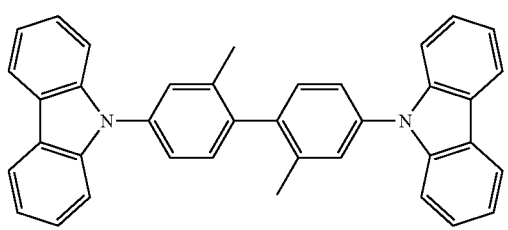

dmCBP

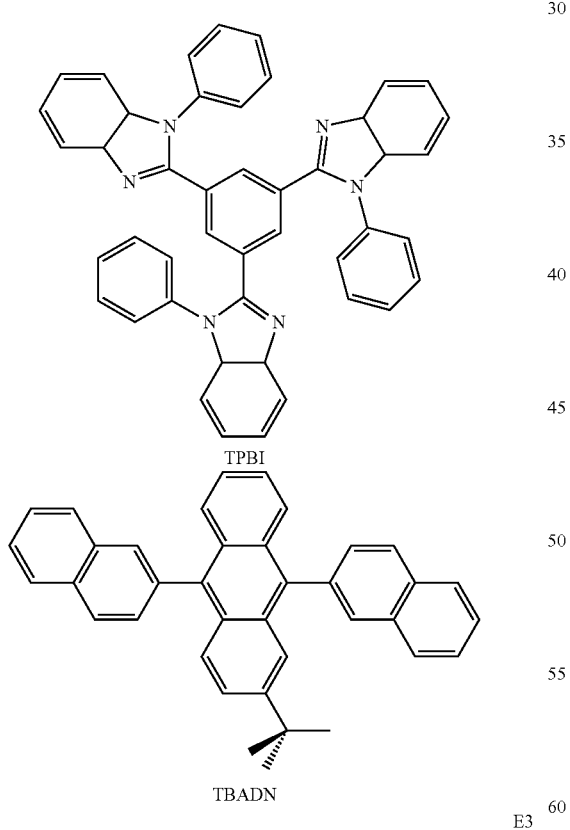

TPBI

TBADN

E3

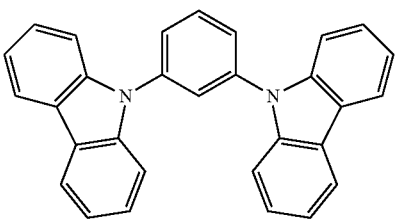

501

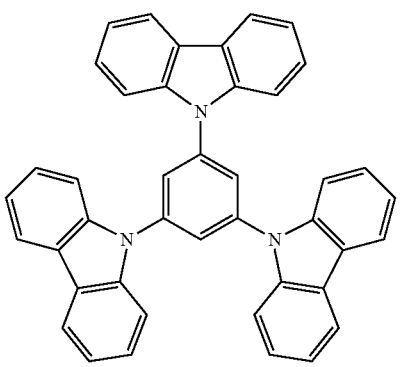

502

-continued
503
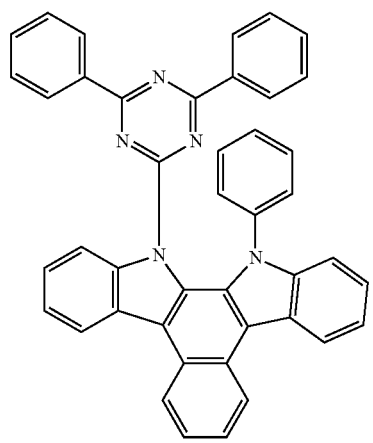
504
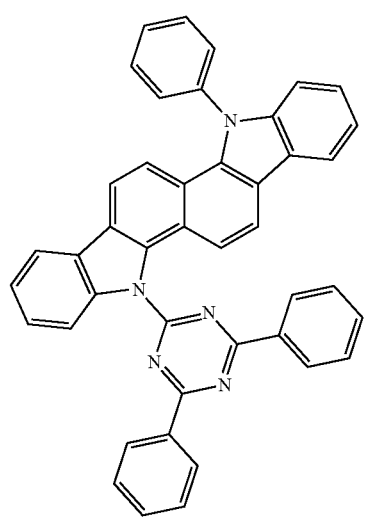
505
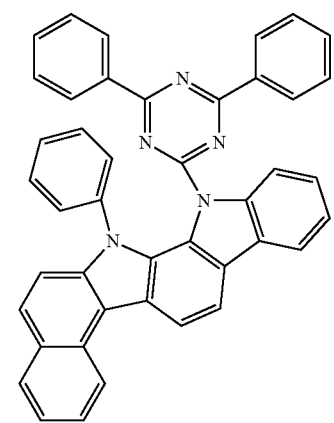
-continued
506
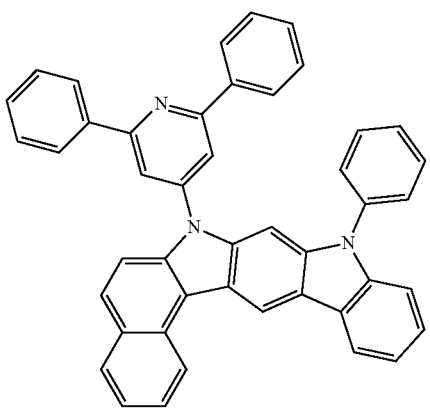
507
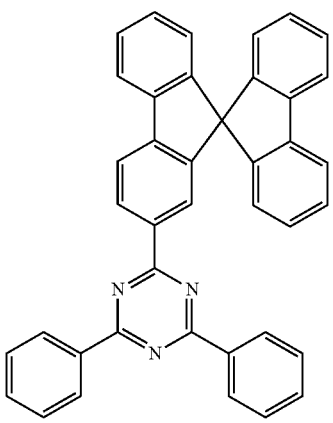
508
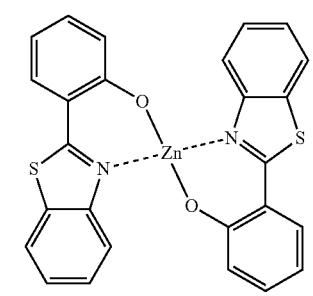
509
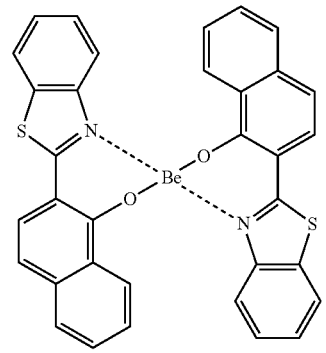

Also, the host may be an anthracene-based compound represented by Formula 400 below:

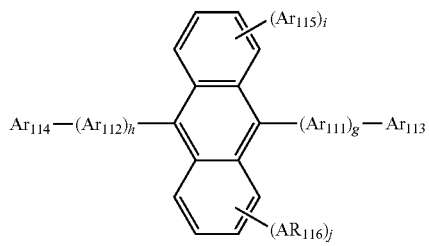

Formula 400

Wherein $Ar_{111}$ and $Ar_{112}$ may be each independently a substituted or unsubstituted $C_5$-$C_{60}$ arylene group; $Ar_{113}$ through $Ar_{116}$ may be each independently a substituted or unsubstituted $C_1$-$C_{10}$ alkyl group or a substituted or unsubstituted $C_5$-$C_{60}$ aryl group; and g, h, i, and j may be each independently an integer of 0 to 4.

For example, in Formula 400 above, $Ar_{111}$ and $Ar_{112}$ may be each independently one of a phenylene group; a naphthylene group; a phenanthrenylene group; a pyrenylene group; and a phenylene group, a naphthylene group, a phenanthrenylene group, a fluorenyl group, and a pyrenylene group that are substituted with at least one of a phenyl group, a naphthyl group, and an anthryl group.

In Formula 400 above, g, h, i, and j may be each independently 0, 1, or 2.

In Formula 400 above, $Ar_{113}$ through $Ar_{116}$ may be each independently, but are not limited to, a $C_1$-$C_{10}$ alkyl group that is substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, and a fluorenyl group; and

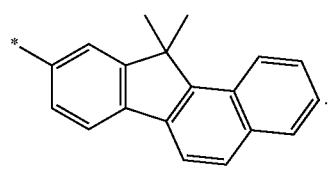 [SMILES: *c1ccc2c(c1)C(C)(C)c1c-2ccc2ccccc12]

For example, the anthracene-based compound of Formula 400 may be, but is not limited to, one of the compounds below:

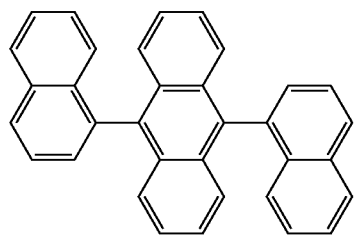

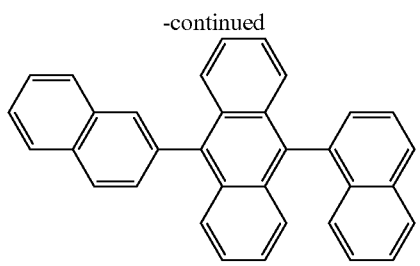

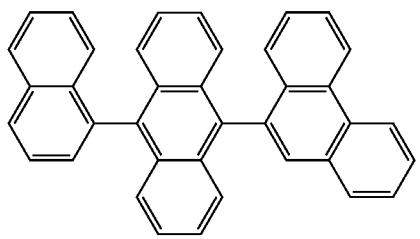

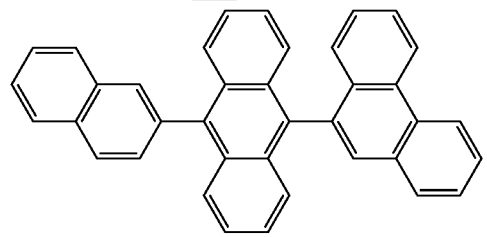

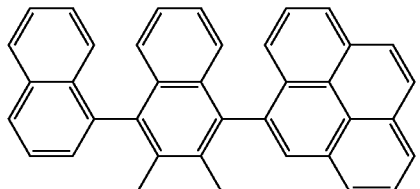

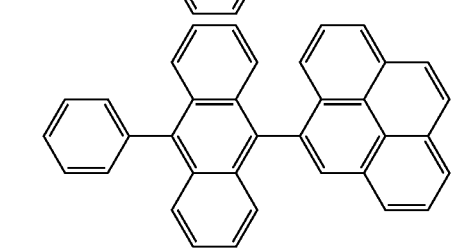

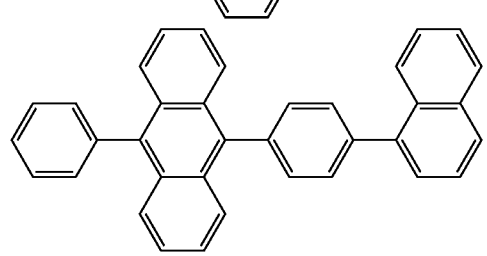

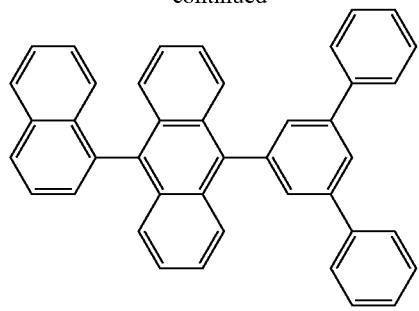
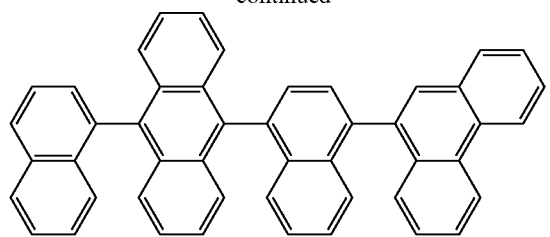
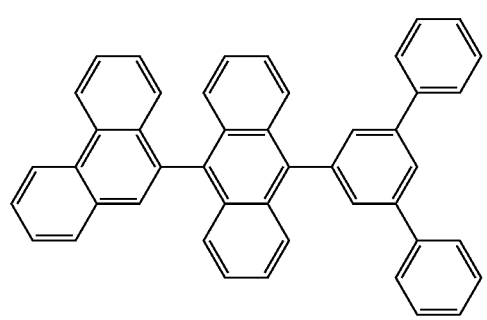
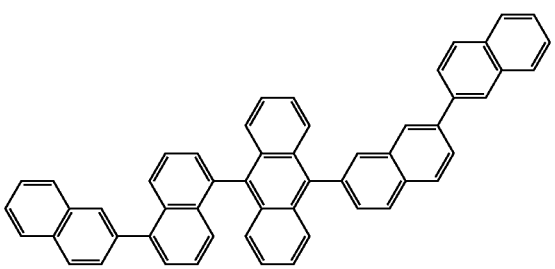
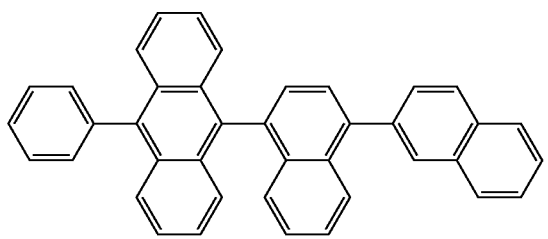
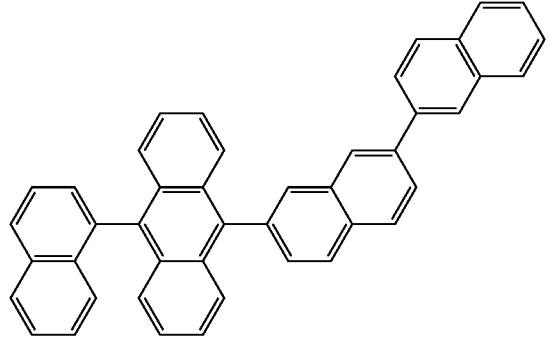
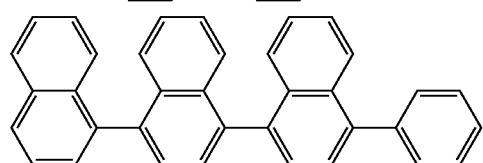
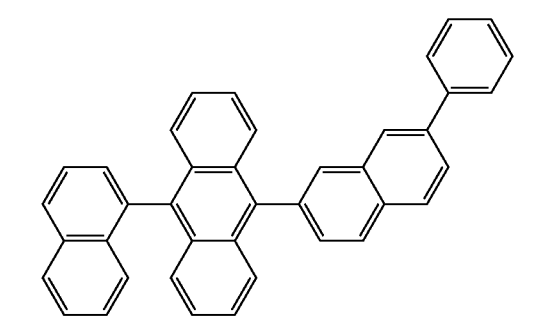
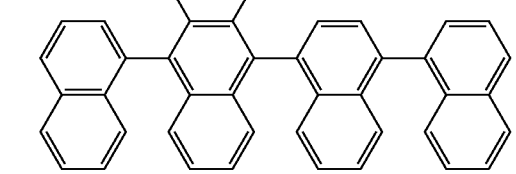
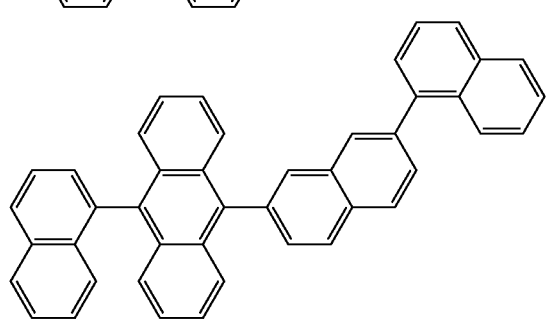
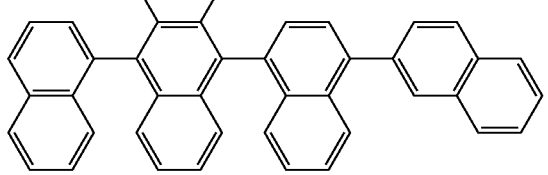

-continued
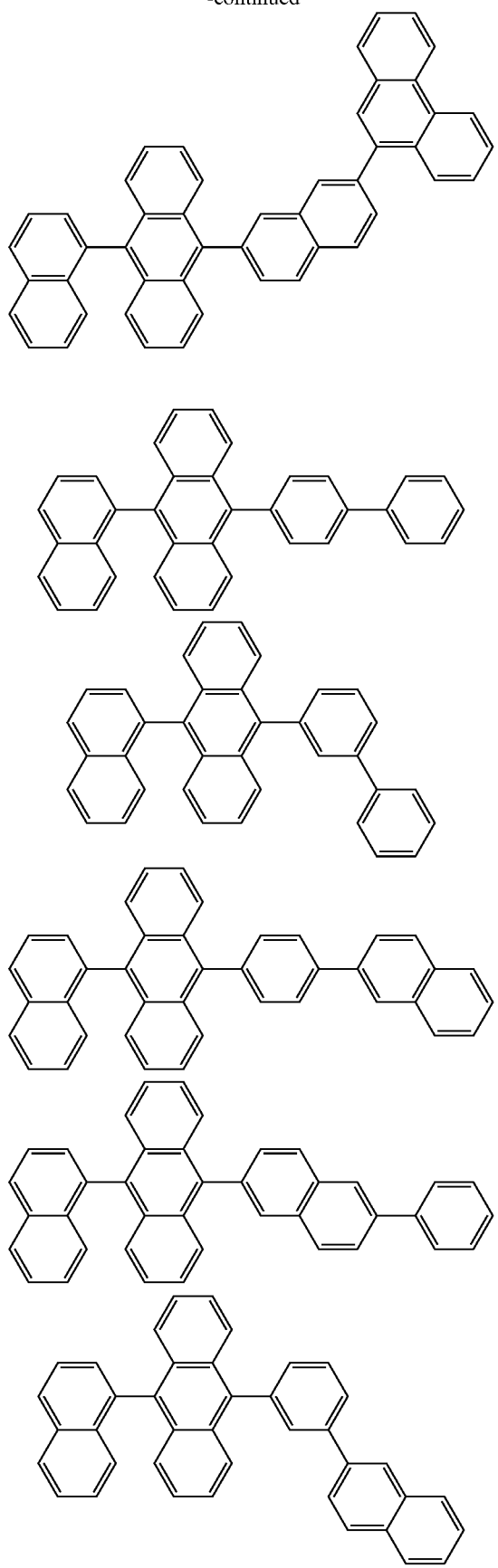
-continued
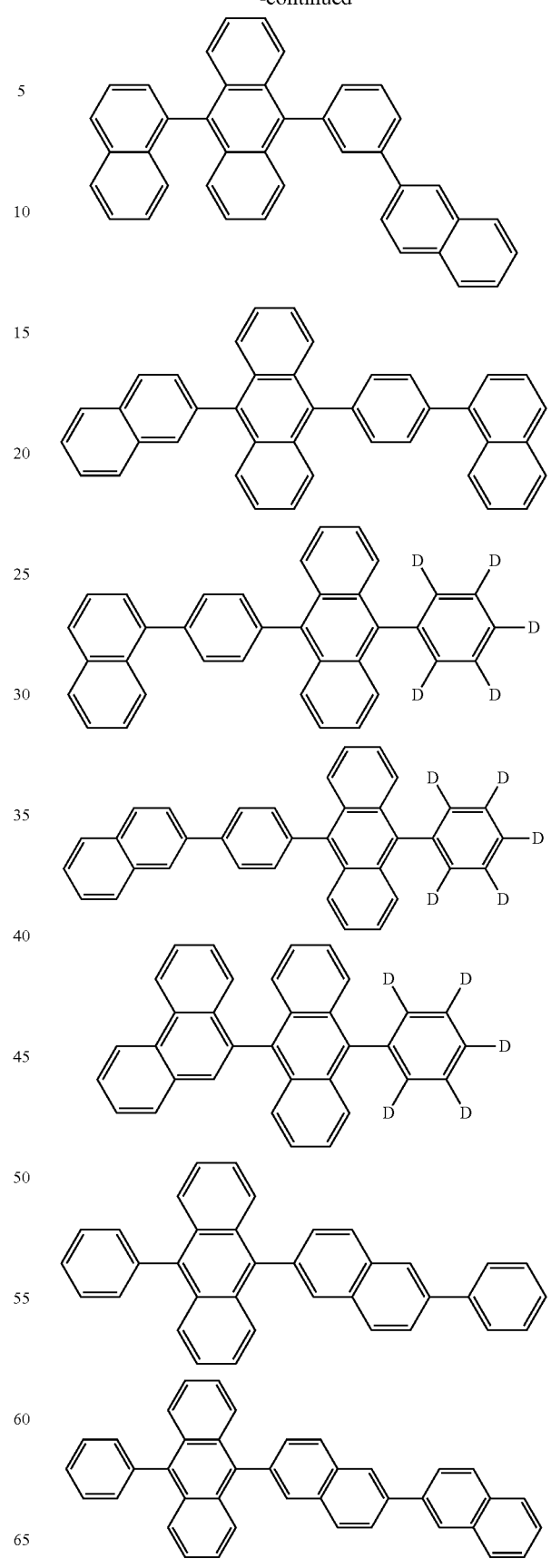

-continued

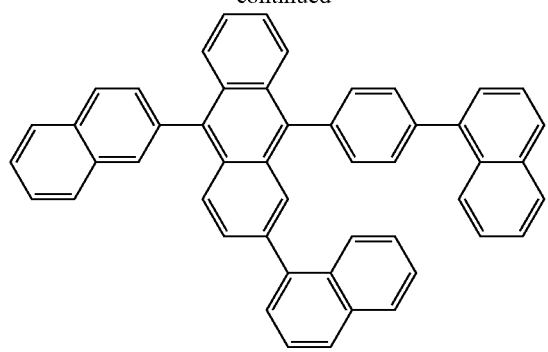
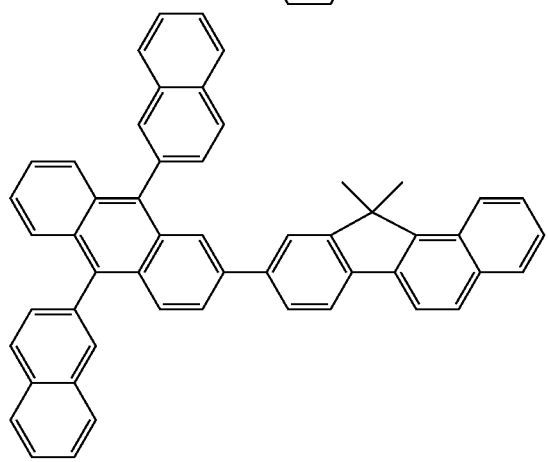
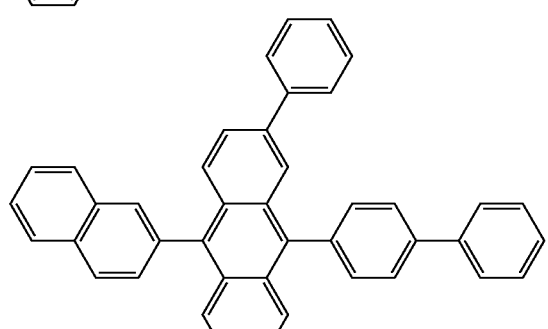
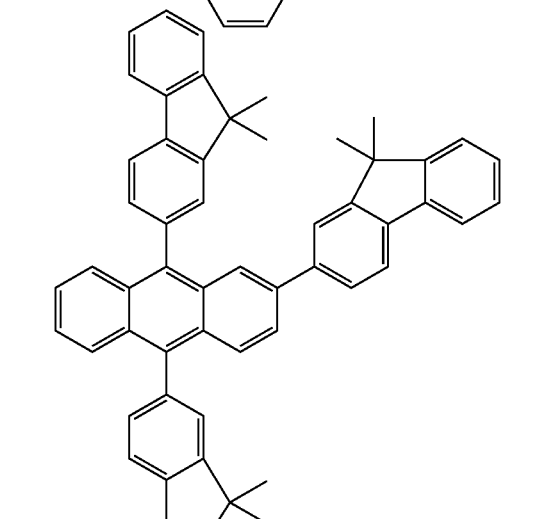

-continued

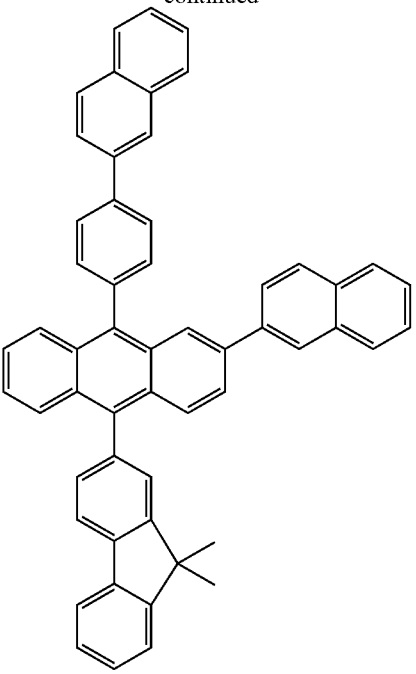
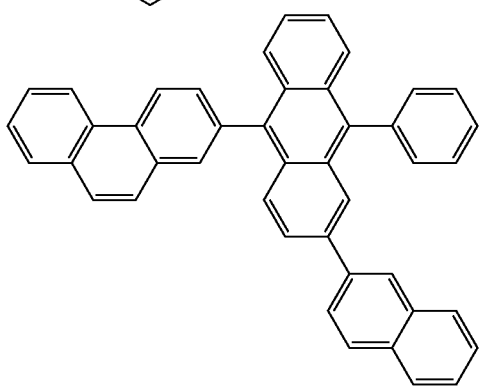

Also, an anthracene-based compound represented by Formula 401 below may be used as the host in the EML:

Formula 401

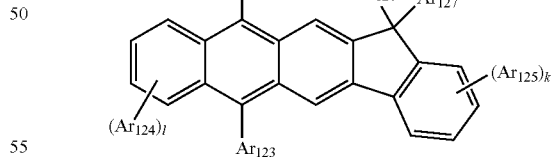

Wherein $Ar_{122}$ through $Ar_{125}$ may be each independently a substituted or unsubstituted $C_1$-$C_{10}$ alkyl group or a substituted or unsubstituted $C_5$-$C_{60}$ aryl group.

In Formula 401 above, $Ar_{126}$ and $Ar_{127}$ may be each independently a $C_1$-$C_{10}$ alkyl group (e.g., a methyl group, an ethyl group, or a propyl group).

In Formula 401 above, k and l may be each independently an integer of 0 to 4. For example, k and l may be each independently 0, 1, or 2.

For example, the anthrecene-based compound of Formula 401 may be, but is not limited to, one of the following compounds:

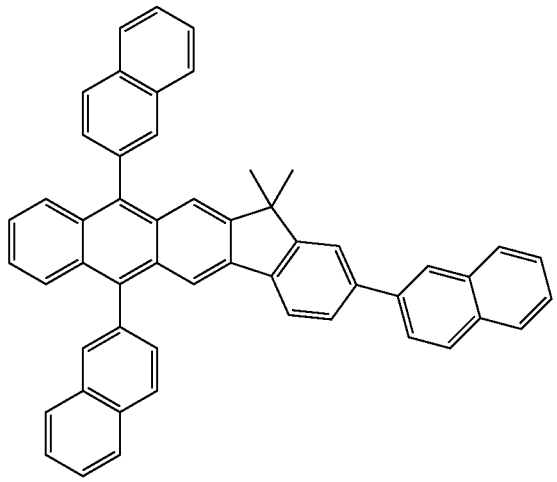

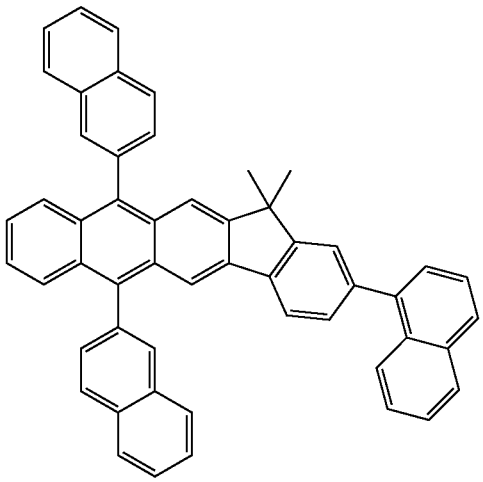

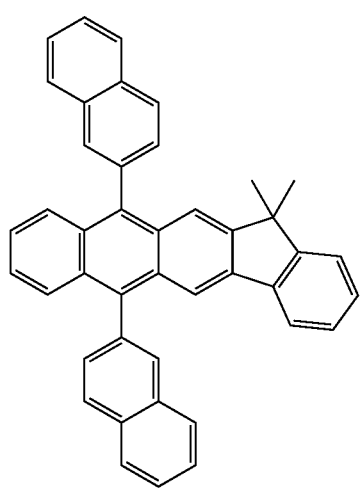

When the organic light-emitting device is a full color organic light-emitting device, the emission layer may be patterned into a red emission layer, a green emission layer, and a blue emission layer. In some embodiments, the emission layer may include at least two of the red emission layer, the green emission layer, and the blue emission layer that are stacked upon one another, or may emit white light, but is not limited thereto.

At least one of the red emission layer, the green emission layer, and the blue emission layer may include a dopant below.

Non-limiting examples of the blue dopant are compounds represented by the following formulae. Herein, ppy means phenylpyridine (ppy=phenylpyridine).

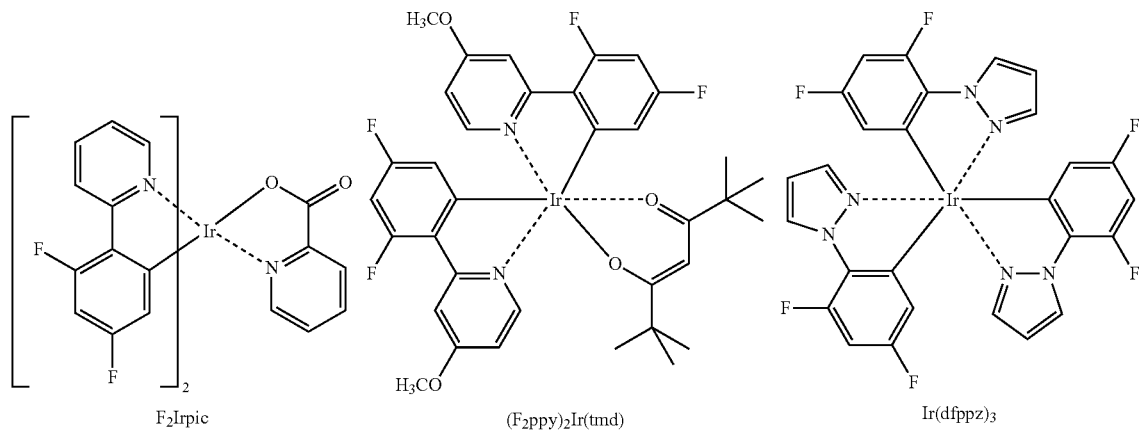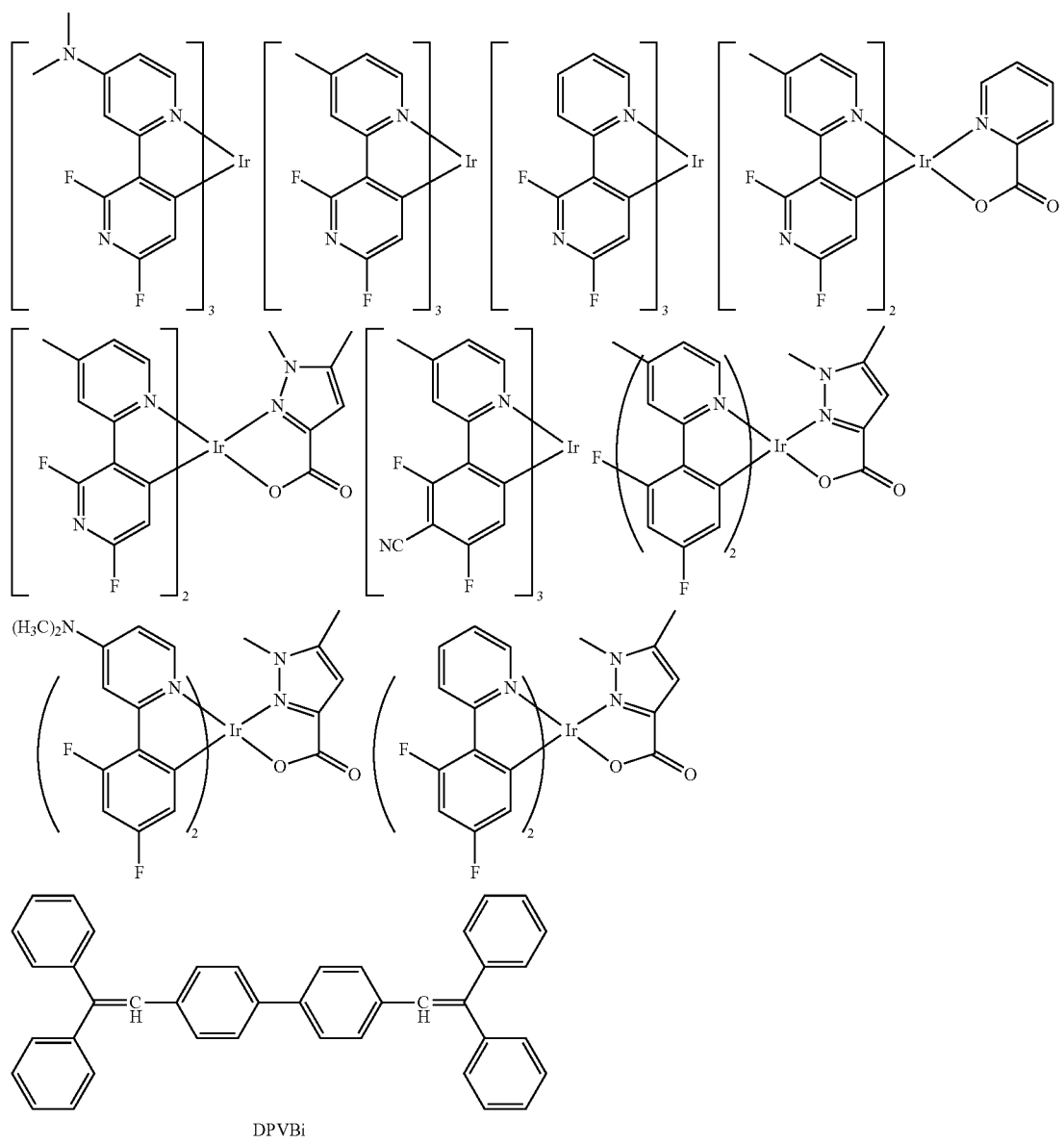

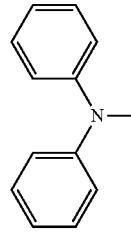
DPAVBi
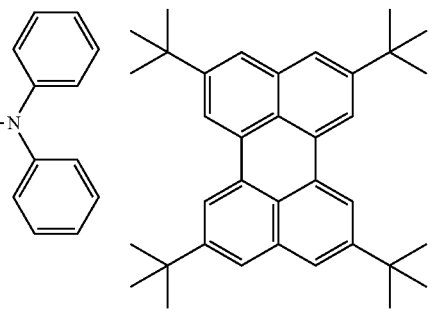
TBPe
Non-limiting examples of the red dopant may be compounds represented by the following formulae. In some embodiments, the red dopant may be DCM or DCJTB, which will be described later.
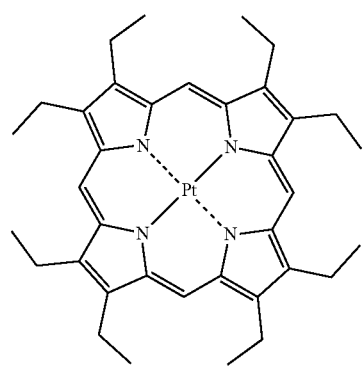
PtOEP
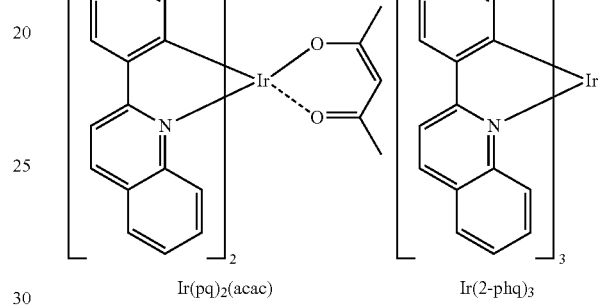
Ir(pq)₂(acac)    Ir(2-phq)₃
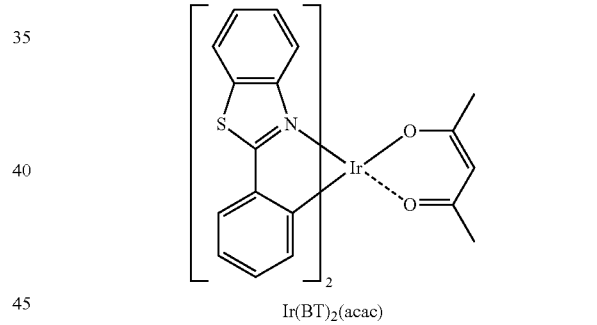
Ir(BT)₂(acac)
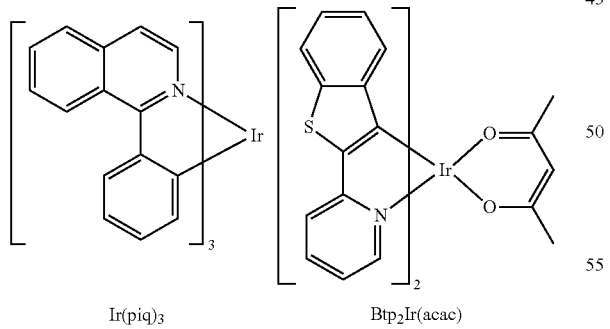
Ir(piq)₃    Btp₂Ir(acac)
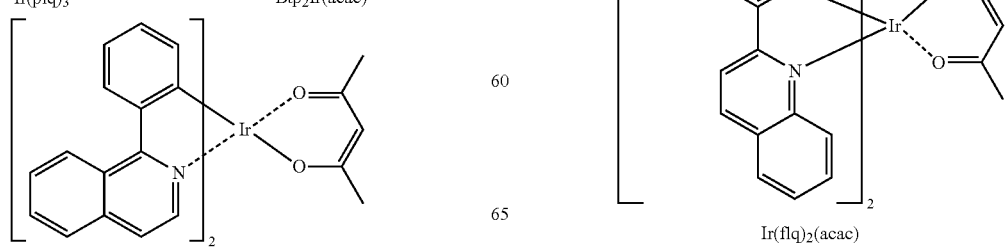
Ir(flq)₂(acac)

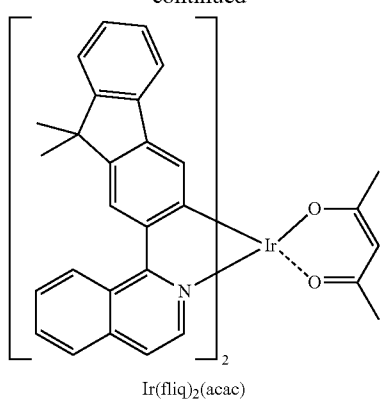
Ir(fliq)₂(acac)
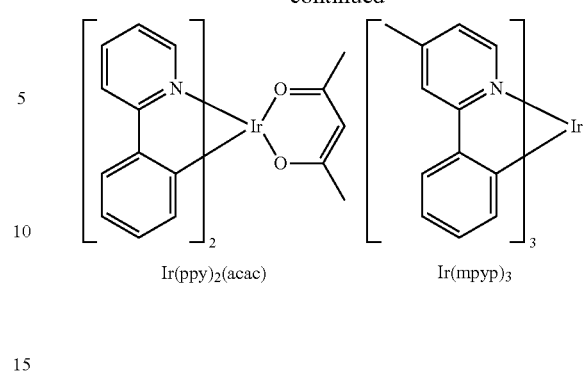
Ir(ppy)₂(acac)　　Ir(mpyp)₃
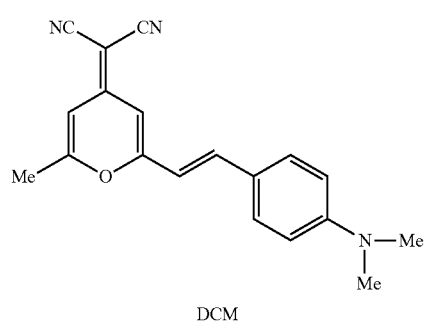
DCM
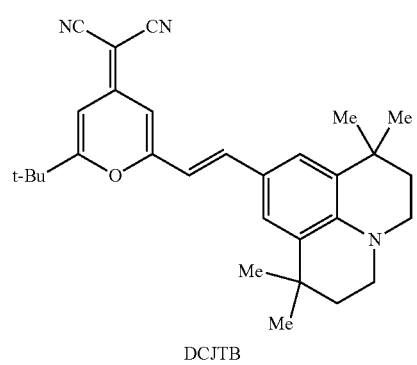 [SMILES: CC(C)(C)C1=CC(=C(C#N)C#N)C=C(/C=C/c2cc3c4c(c2)C(C)(C)CCN4CCC3(C)C)O1]
DCJTB
Non-limiting examples of the green dopant may be compounds represented by the following formulae. In an embodiment, the green dopant may be C545T represented below.
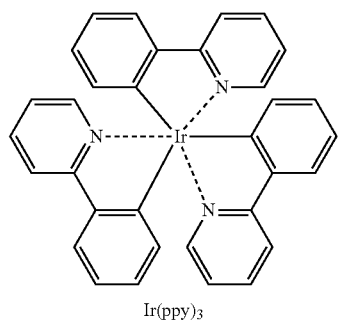
Ir(ppy)₃
C545T
Non-limiting examples of the dopant that may be used in the EML may be complexes represented by the following formulae.
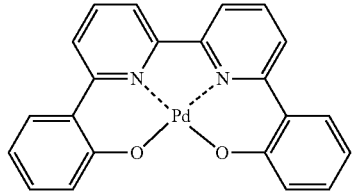
D1
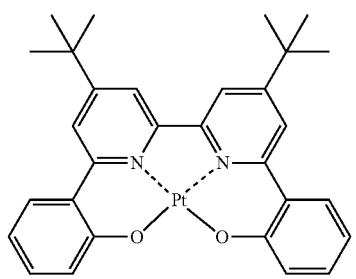
D2
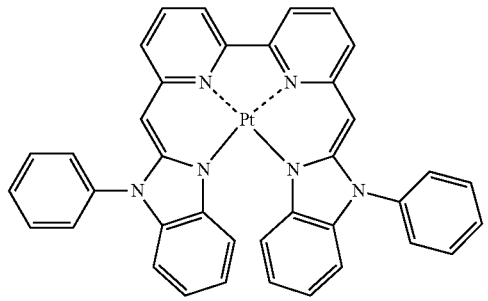
D3

D4
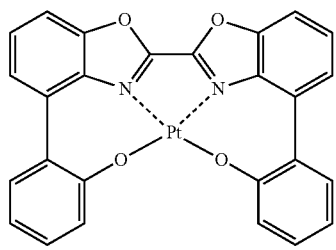
D5
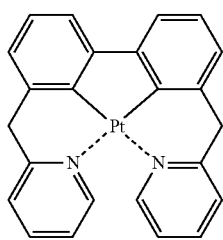
D6
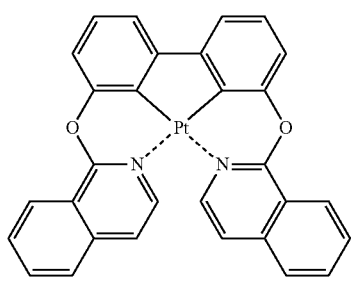
D7
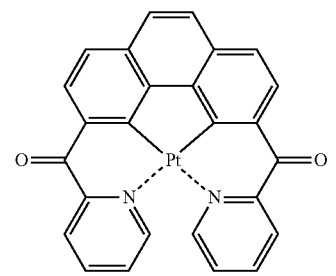
D8
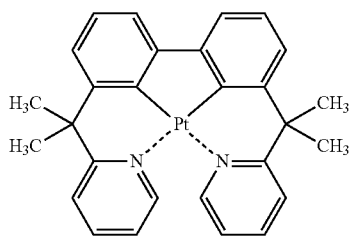
D9
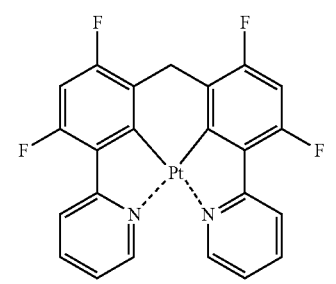
D10
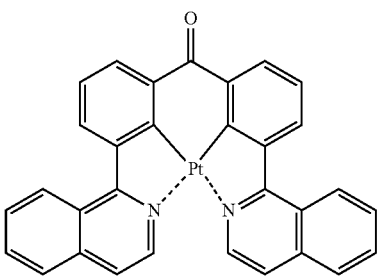
D11
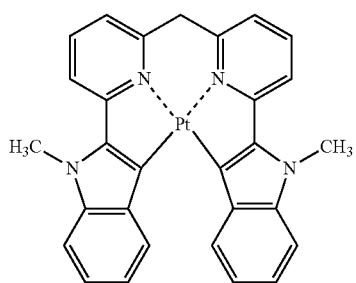
D12
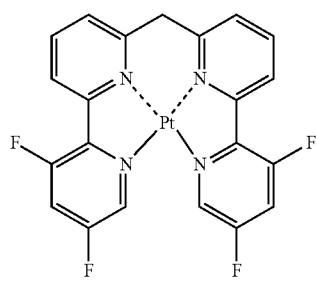
D13
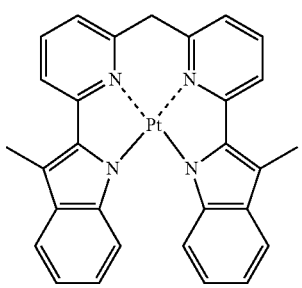
D14
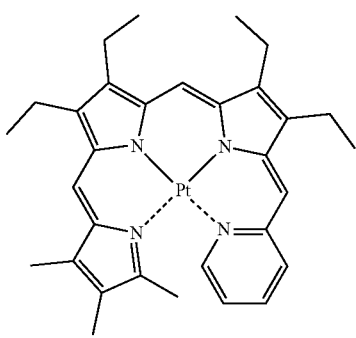

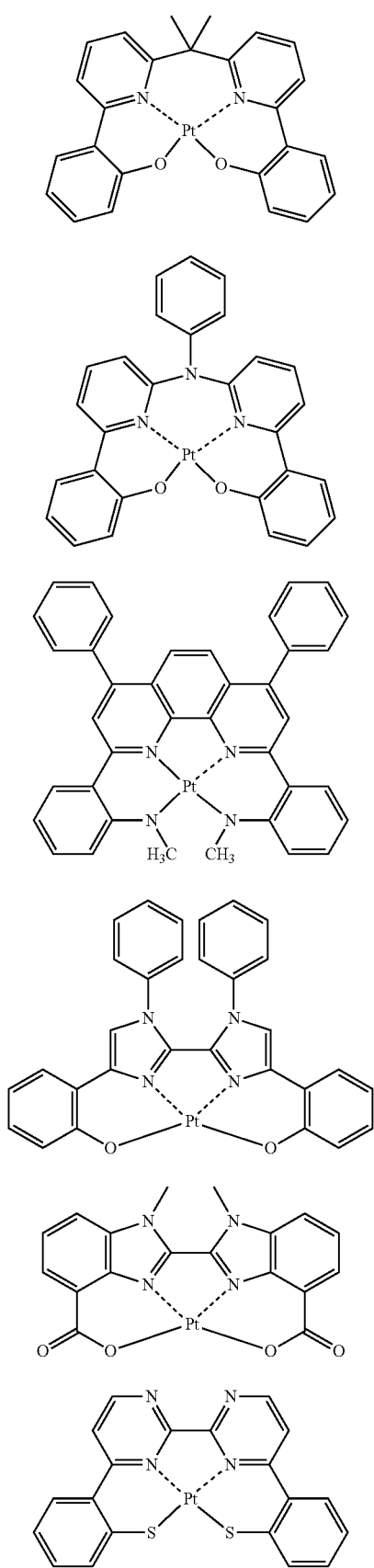

-continued
D26 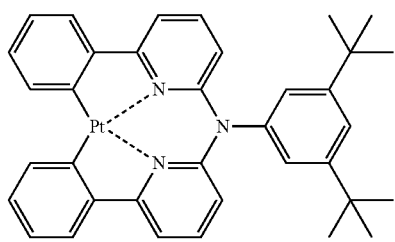
D27 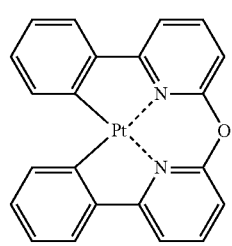
D28 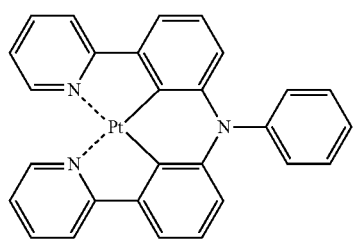
D29 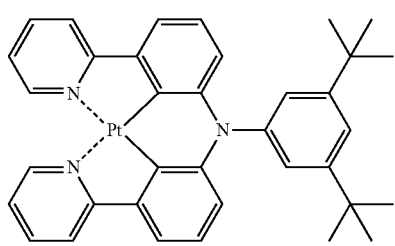
D30 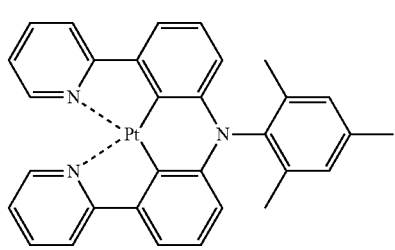
D31 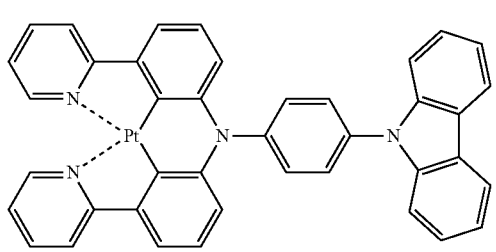
-continued
D32 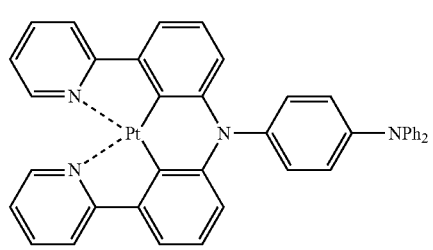
D33 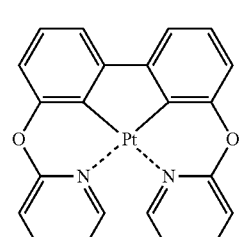
D34 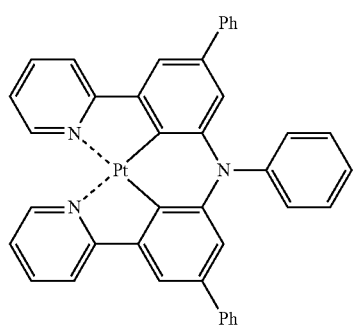
D35 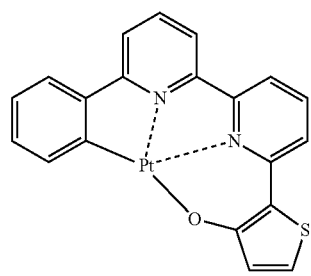
D36 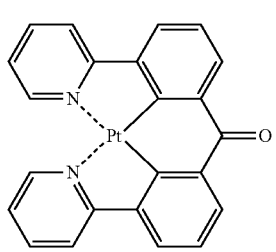

D37
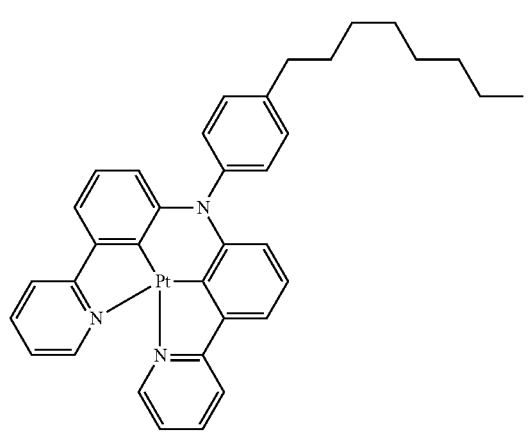
D38
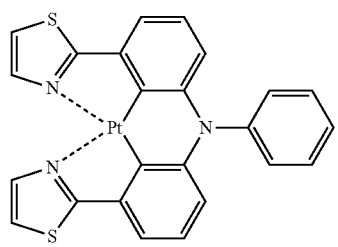
D39
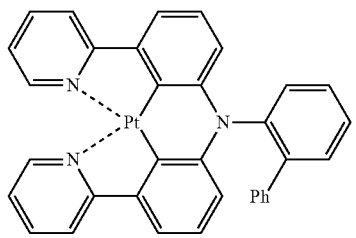
D40
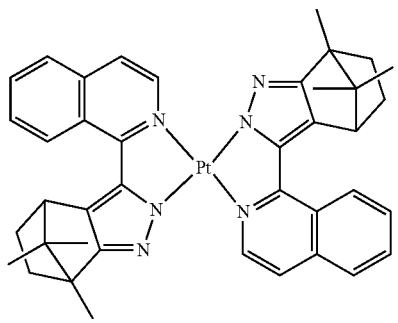
D41
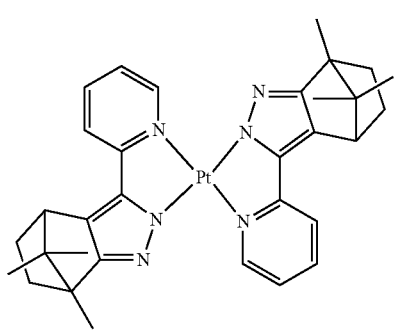
D42
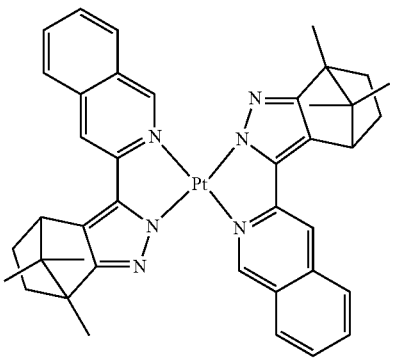
D43
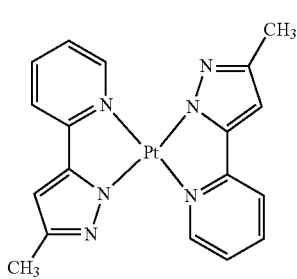
D44
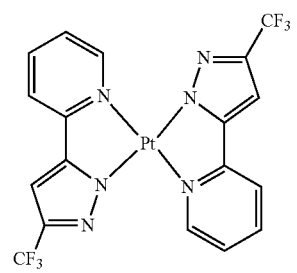
D45
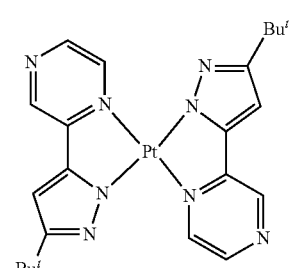
D46
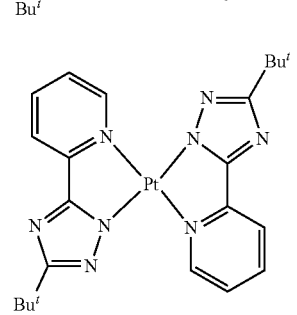

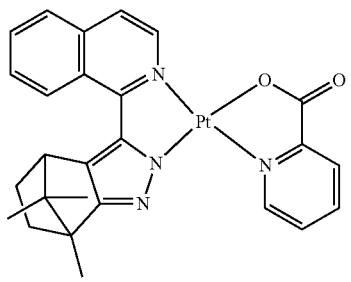

D47

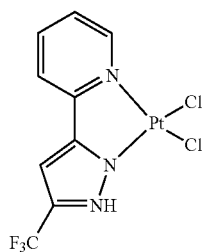

D48

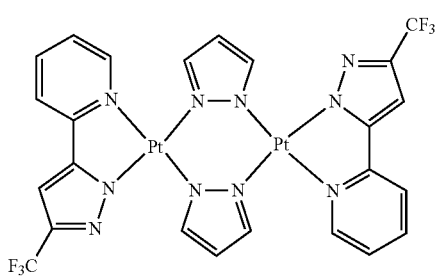

D49

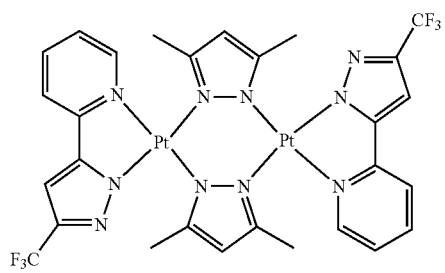

D50

Non-limiting examples of the dopant that may be used in the EML may be Os complexes represented by the following formulae.

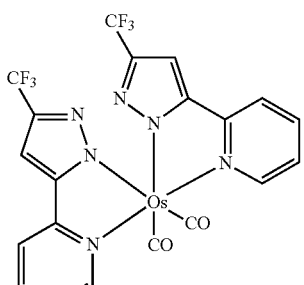

Os(fppz)$_2$(CO)$_2$

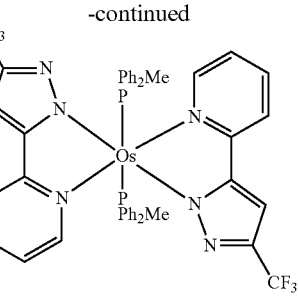

Os(fppz)$_2$(PPh$_2$Me)$_2$

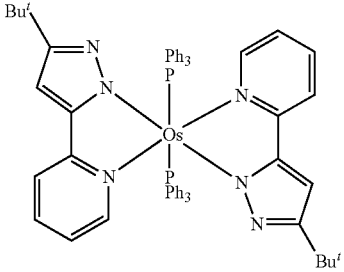

Os(bppz)$_2$(PPh$_3$)$_2$

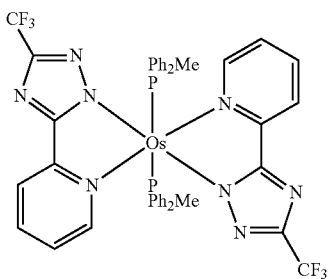

Os(fptz)$_2$(PPh$_2$Me)$_2$

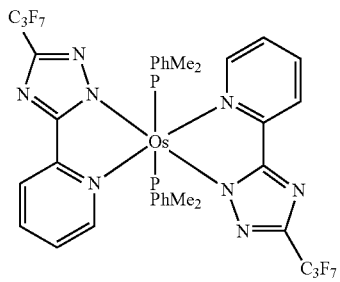

Os(hptz)$_2$(PPhMe$_2$)$_2$

When the EML includes both a host and a dopant, the amount of the dopant may be from about 0.01 to about 15 parts by weight based on 100 parts by weight of the host. However, the amount of the dopant is not limited to this range.

The thickness of the EML may be about 100 Å to about 1000 Å, and in some embodiments, may be from about 200 Å to about 600 Å. When the thickness of the EML is within these ranges, the EML may have good light emitting ability without a substantial increase in driving voltage.

When a phosphorescent dopant is also used in the EML, a hole blocking layer (HBL) may be formed on the EML by using vacuum deposition, spin coating, casting, Langmuir-Blodgett (LB) deposition, or the like, in order to prevent diffusion of triplet excitons or holes into an ETL. When the HBL is formed using vacuum deposition or spin coating, the conditions for deposition and coating may be similar to those for the formation of the HIL, although the conditions for deposition and coating may vary according to the material that is used to form the HBL. The phosphine oxide-based compound of Formula 1 above may be used as a material for the HBL.

A thickness of the HBL may be from about 20 Å to about 1000 Å, and in some embodiments, may be from about 30 Å to about 800 Å. When the thickness of the HBL is within these ranges, the HBL may have improved hole blocking ability without a substantial increase in driving voltage.

Then, an ETL may be formed on the EML or HBL by any of a variety of methods, for example, vacuum deposition, spin coating, or casting. When the ETL is formed using vacuum deposition or spin coating, the deposition and coating conditions may be similar to those for the formation of the HIL, though the deposition and coating conditions may vary according to a material that is used to form the ETL. The phosphine oxide-based compound of Formula 1 above may be used as a material for the ETL. In some embodiments, when the phosphine oxide-based material of Formula 1 above is used in the HBL, any known electron transporting material that can stably transport electrons injected from an electron injecting electrode (cathode) may be used as a material for the ETL. Non-limiting examples of materials for forming the ETL may be a quinoline derivative, such as tris(8-quinolinorate)aluminum (Alq3), TAZ, BAlq, beryllium bis(benzoquinolin-10-olate (Bebq2), 9,10-di(naphthalene-2-yl)anthracene (ADN), BCP, Compound 201, and Compound 202, but are not limited thereto.

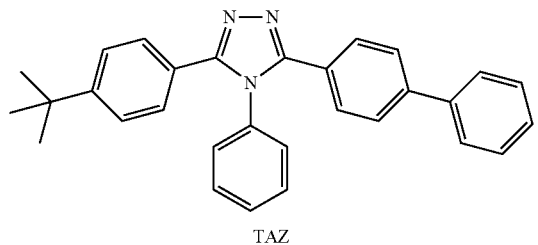

TAZ

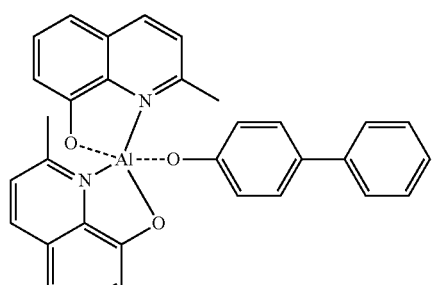

BAlq

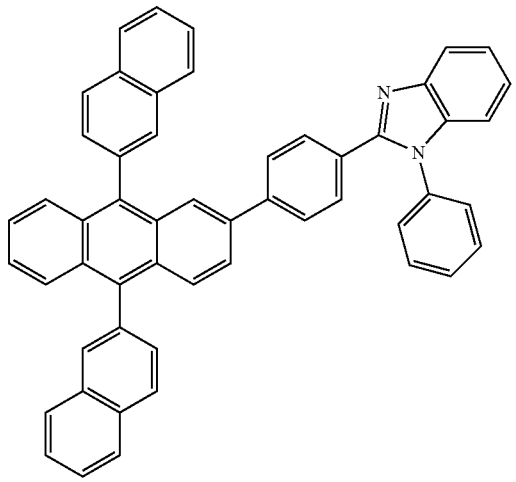

Compound 201

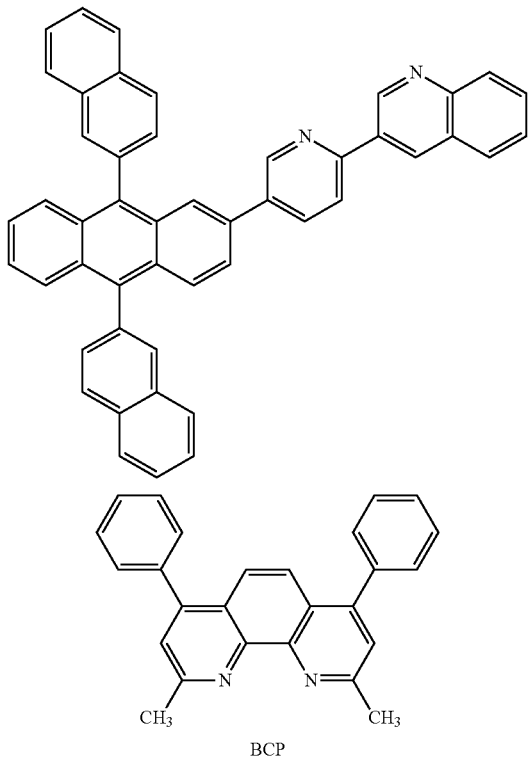

Compound 202

BCP

A thickness of the ETL may be from about 100 Å to about 1,000 Å, and in some embodiments, may be from about 150 Å to about 500 Å. When the thickness of the ETL is within these ranges, the ETL may have satisfactory electron transporting ability without a substantial increase in driving voltage.

In some embodiments the ETL may further include a metal-containing material, in addition to any known electron-transporting organic compound.

The metal-containing compound may include a lithium (Li) complex. Non-limiting examples of the Li complex May be lithium quinolate (LiQ) and Compound 203 below:

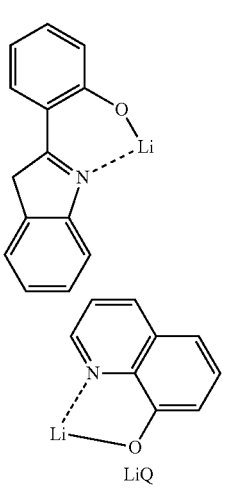

Compound 203

LiQ

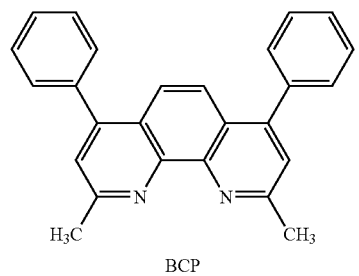

BCP

Then, an EIL, which facilitates injection of electrons from the cathode, may be formed on the ETL. Any suitable electron-injecting material may be used to form the EIL.

Non-limiting examples of the material for forming the EIL may be LiF, NaCl, CsF, $Li_2O$, and BaO, which are known in the art. The deposition and coating conditions for forming the EIL may be similar to those for the formation of the HIL, though the deposition and coating conditions may vary according to the material that is used to form the EIL.

A thickness of the EIL may be from about 1 Å to about 100 Å, and in some embodiments, may be from about 3 Å to about 90 Å. When the thickness of the EIL is within these ranges, the EIL may have satisfactory electron injection ability without a substantial increase in driving voltage.

The second electrode 17 is disposed on the organic layer 15. The second electrode 17 may be a cathode that is an electron injection electrode. A material for forming the second electrode 17 may be a metal, an alloy, an electro-conductive compound, which have a low work function, or a mixture thereof. In this regard, the second electrode 17 may be formed of lithium (Li), magnesium (Mg), aluminum (Al), aluminum-lithium (Al—Li), calcium (Ca), magnesium-indium (Mg—In), magnesium-silver (Mg—Ag), or the like, and may be formed as a thin film type transmission electrode. In some embodiments, to manufacture a top-emission light-emitting device, the transmission electrode may be formed of indium tin oxide (ITO) or indium zinc oxide (IZO).

Although the organic light-emitting device of FIG. 1 is described above, the present invention is not limited thereto.

Also, when a phosphorescent dopant is included in the EML, a HBL may be formed between the ETL and the EML or between the H-functional layer and the EML by vacuum deposition, spin coating, casting or LB deposition so as to prevent triplet excitons or holes from being diffused to the ETL. When the HBL is formed by vacuum deposition or spin coating, the conditions thereof may vary according to a used compound. However, in general, the deposition and coating conditions may be almost the same as the condition for forming the HIL. The HBL may include a known hole blocking material. Examples of the known hole blocking material may include an oxadiazole deriative, a triazole derivative, and a phenanthroline derivative. For example, BCP may be used as a hole blocking material.

The thickness of the HBL may be in the range of about 20 Å to about 1,000 Å. In some embodiments, the thickness of the HBL may be in the range of about 30 Å to about 300 Å. When the thickness of the HBL is within these ranges, excellent hole blocking properties may be obtained without a substantial increase in driving voltage.

Hereinafter, the present invention will be described in detail with reference to the following synthesis examples and other examples. However, these examples are for illustrative purposes only and are not intended to limit the scope of the present invention.

EXAMPLE

Synthesis Example 1

Synthesis of Compound 1

Compound 1 was synthesized according to Reaction Scheme 1 below:

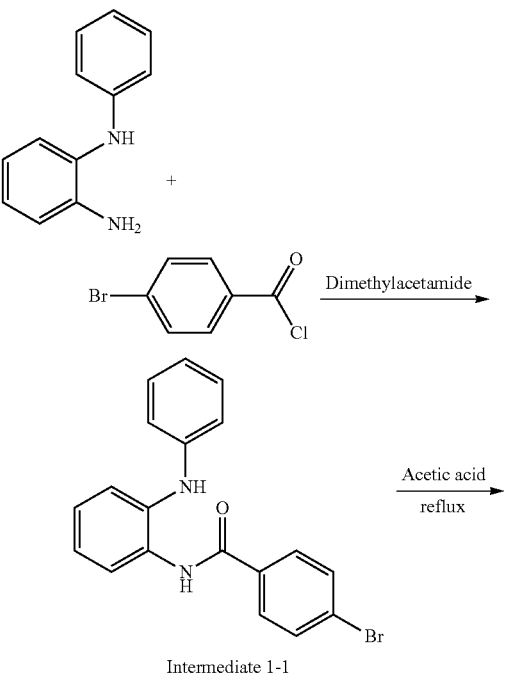

Reaction Scheme 1

Intermediate 1-1

-continued

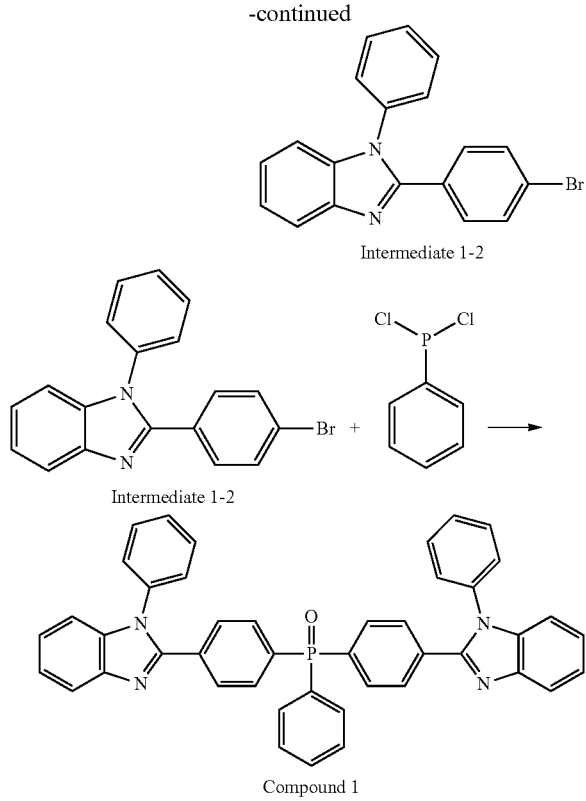

Intermediate 1-2

Compound 1

Synthesis of Intermediate 1-1

25 g (114 mmol) of 4-bromo benzoyl chloride and 40 mL of diethyl acetamide were put in a 500-mL 3-necked round flask, and stirred for about 30 minutes. Subsequently, a solution of 2-aminodiphenyl amine (21 g, 114 mmol) dissolved in 100 mL of diethyl acetamide was slowly dropwise added into the reaction vessel and stirred for about 2 hours, followed by an addition of 800 mL of $H_2O$ to terminate the reaction. The resulting solid compound was washed with water and methanol, recrystallized in a DMF/$H_2O$ condition, and then identified using nuclear magnetic resonance spectroscopy ($^1$H NMR).

Yield: 31.4 g, 75%

$^1$H NMR (300 MHz, CD2Cl2, δ): 8.33 (s, 1H), 8.19-8.16 (d, 1H), 7.56-7.51 (m, 4H), 7.32-7.20 (m, 5H), 6.91-6.82 (m, 3H), 5.73 ppm (s, 1H).

Synthesis of Intermediate 1-2

31.4 g (85.5 mmol) of Intermediate 1-1 was dissolved in 120 mL of acetic acid in a 500-mL 3-necked round flask, and refluxed at about 100° C. for about 12 hours. After termination of the reaction, distillation at a reduced pressure was performed to remove acetic acid, followed by washing four times each with 100 mL of water, and drying the resulting solid compound under a reduced pressure, thereby obtaining Intermediate 1-2, which was identified using $^1$H NMR.

Yield: 27.9 g, 93%

$^1$H NMR (300 MHz, CD2Cl2, δ): 7.86-7.83 (d, 1H), 7.56-7.55 (m, 3H), 7.48 (s, 4H), 7.37-7.28 ppm (m, 5H).

Synthesis of Compound 1

10 g (28.6 mmol) of Intermediate 1-2 and 100 mL of tetrahydrofuran (THF) were put in 500-mL 3-necked round flask, and stirred for about 20 minutes to obtain a reaction mixture, which was maintained at a temperature of about −78° C. using a cooling/warm-up bath (Acetone/Liq-$N_2$ bath), followed by an addition of n-BuLi (2.5 M, 11.9 mL, 29.9 mmol). The resulting reaction mixture was stirred for about 2 hours while being purged with nitrogen, followed by adding 2.32 g (13.0 mmol) of dichlorophenyl phosphine, slowly increasing the temperature to room temperature, and stirring the reaction mixture for about 24 hours. 30 mL of $H_2O$ was added into the resulting mixture to terminate the reaction, followed by extraction twice each with 500 mL of $CH_2Cl_2$, drying with anhydrous magnesium sulfate ($MgSO_4$), and distillation under a reduced pressure. The resulting product was oxidized using $CH_2Cl_2$ and 30% $H_2O_2$, and subjected to column chromatography (MeOH/EA; 1/20) to isolate Compound 1, which was identified using $^1$H NMR and mass spectroscopy.

Yield: 1.22 g, 15%

$^1$H NMR (300 MHz, CD2Cl2, δ): 7.70-7.69 (d, 2H), 7.62-7.54 (m, 19H), 7.37-7.30 ppm (m, 10H): HRMS (FAB+): calcd for C44H31N4OP, 662.2235. found, (M+H) 663.2310.

Evaluation Example 1

Characteristics Evaluation of Compound 1

Evaluation of Thermal Characteristics of Compound 1

Figure 2:
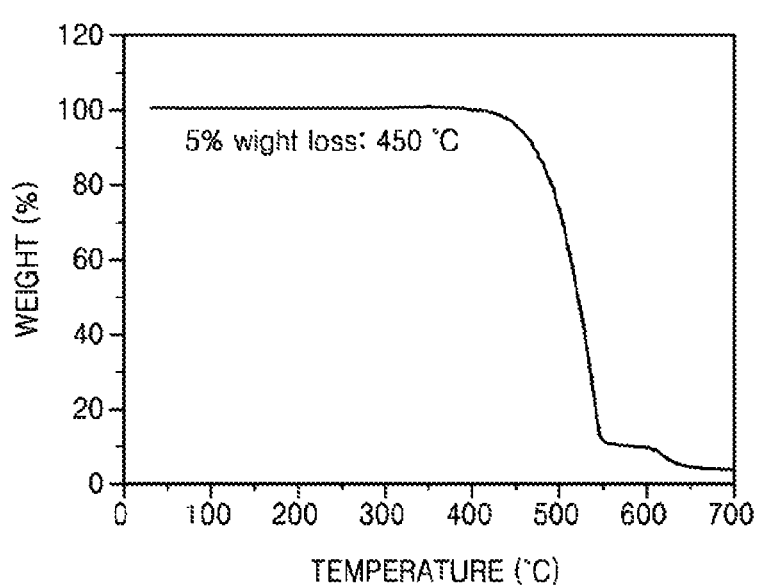
FIG. 2 is a graph showing thermogravimetric analysis (TGA) data of Compound 1 according to an embodiment of the present invention.
Figure 3:
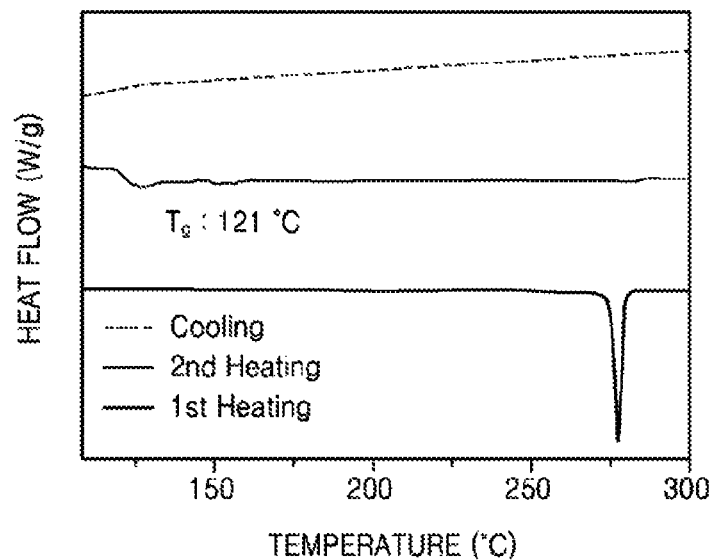
FIG. 3 is a graph showing differential scanning calorimetric (DSC) data of Compound 1 according to an embodiment of the present invention.

Thermal analysis of Compound 1 was performed using thermo gravimetric analysis (TGA) and differential scanning calorimetry (DSC) ($N_2$ atmosphere, temperature range: room temperature to 600° C. (10° C./min)-TGA, room temperature to 400° C.-DSC, Pan Type Pt Pan in disposable Al Pan (TGA), disposable Al pan (DSC)). The results are shown in FIGS. 2 and 3. Referring to FIGS. 2 and 3, Compound 1 is found to have improved thermal stability.

Evaluation of Spectroscopic Characteristics of Compound 1

Figure 4:
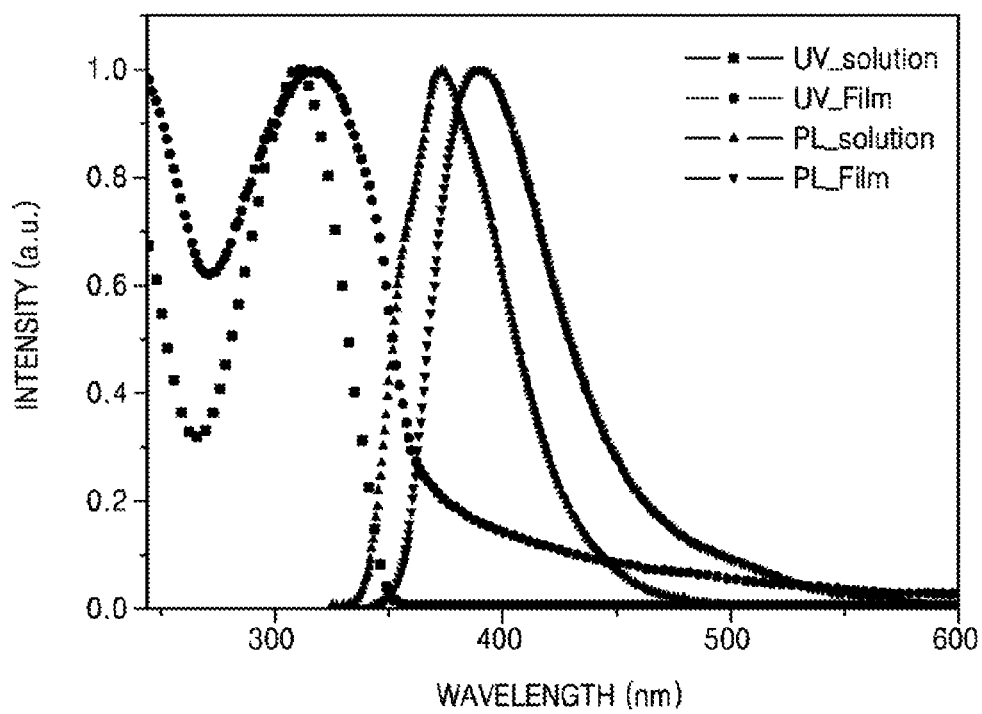
FIG. 4 is a graph showing spectroscopic analysis data of Compound 1 according to an embodiment of the present invention.

UV absorption and photoluminescence (PL) spectra of Compound 1 were evaluated. The results are shown in FIG. 4. Four different graphs in FIG. 4 were obtained using the following methods as shown in Table 1:

TABLE 1

| | |
|---|---|
| "UV_solution" graph | Compound 1 was diluted in $CHCl_3$ to a concentration of $1 \times 10^{-5}$M, and then UV absorption spectra thereof were measured using a Shimadzu UV-350 Spectrometer. |
| "UV_film" graph | The dilution of Compound 1 in $CHCl_3$ to a concentration of $1 \times 10^{-5}$M was coated on a glass substrate, followed by thermal treatment at a temperature of about 70° C. to remove solvent. Subsequently, the resulting film was subjected to UV absorption spectrum measurement using a Shimadzu UV-350 Spectrometer. |
| "PL_solution" graph | The dilution of Compound 1 in $CHCl_3$ to a concentration of $1 \times 10^{-5}$M was subjected to photoluminescence (PL) spectrum measurement using an ISC PC1 Spectrofluorometer equipped with a Xenon lamp. |
| "PL_film" graph | The dilution of Compound 1 in $CHCl_3$ to a concentration of $1 \times 10^{-5}$M was coated on a glass substrate, followed by thermal treatment at a temperature of about 70° C. to remove solvent. Subsequently, the resulting film was subjected to PL spectrum measuremen using an ISC PC1 Spectrofluorometer equipped with a Xenon lamp. |

UV absorption peak wavelengths and PL peak wavelengths of Compound 1 in FIG. 4 are summarized in Table 2 below:

TABLE 2

| UV absorption peak wavelength$_{max}$ (nm) | | PL peak wavelength$_{max}$ (nm) | |
|---|---|---|---|
| UV_solution | UV_film | PL_solution | PL_film |
| 311 | 318 | 373 | 389 |

Referring to FIG. 4 and Table 2 above, Compound 1 is found to have appropriate spectroscopic characteristics for use as a material for organic light-emitting devices.

Evaluation of Electrochemical Characteristics of Compound 1

Electrochemical characteristics of Compound 1 were measured using cyclic voltammetry (CV) (Electrolyte: 0.1 M Bu$_4$NClO$_4$/Solvent: CH$_2$Cl$_2$/Electrode: 3-electrode system (working electrode: GC, reference electrode: Ag/AgCl, auxiliary electrode; Pt)). The results are shown in FIG. 5.

Evaluation of HOMO and LUMO Energy Levels of Compound 1

Figure 5:
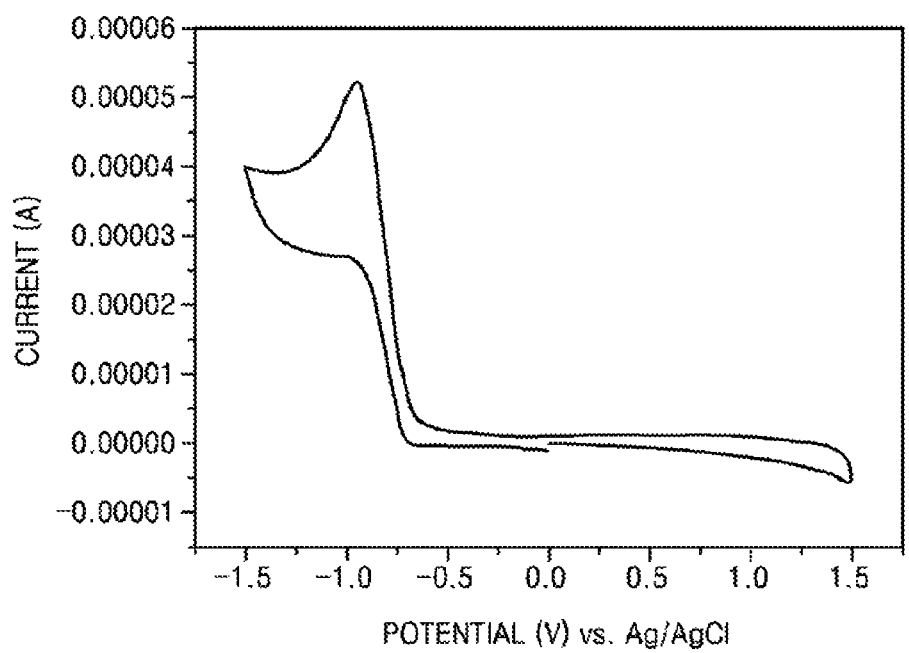
FIG. 5 is a graph showing cyclic voltametric analysis data of Compound 1 according to an embodiment of the present invention.

A lowest unoccupied molecular orbital (LUMO) energy level of Compound 1 was calculated using a reduction onset in FIG. 5. A highest occupied molecular orbital (HOMO) energy level of Compound 1 was calculated using an optical band gap (Eg) based on the UV absorption edge in FIG. 4. The results are shown in Table 3.

TABLE 3

| HOMO(eV) | LUMO(eV) | Eg(eV) |
|---|---|---|
| −7.07 | −3.72 | 3.35 |

Synthesis Example 2

Synthesis of Compound 2

Compound 2 was synthesized according to Reaction Scheme 2 below:

Reaction Scheme 1

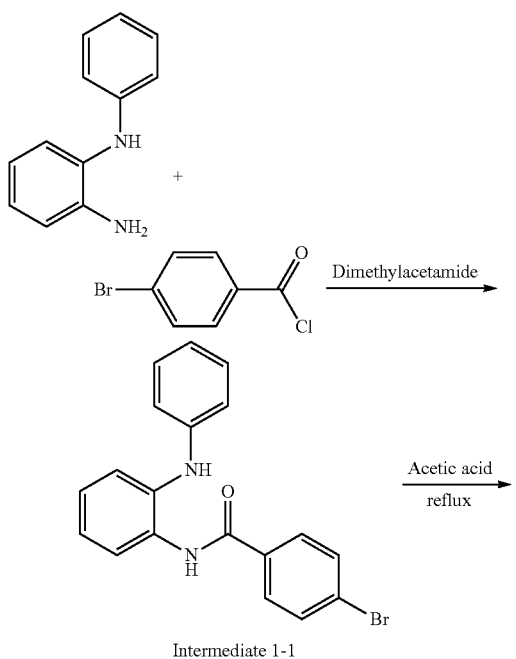

Intermediate 1-1

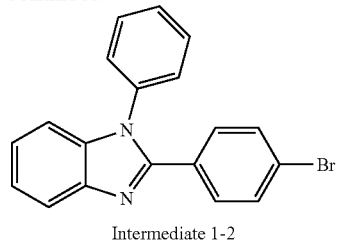

Intermediate 1-2

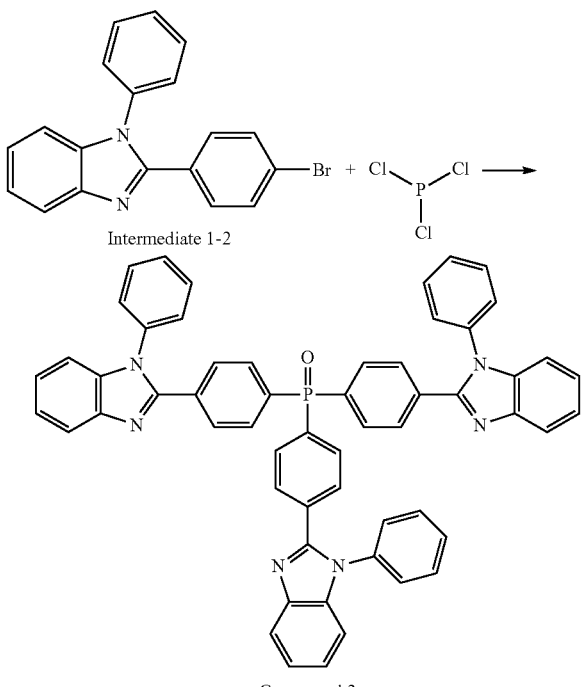

Compound 2

Compound 2 was synthesized in the same manner as in Synthesis Example 1, except that 1.23 g (8.94 mmol) of trichlorophosphine, instead of dichlorophenylphosphine used to synthesize Compound 1, was used. Compound 2 was identified using $^1$H NMR and mass spectroscopy.

Yield: 3.33 g, 42%

$^1$H NMR (300 MHz, CD$_2$Cl$_2$, δ): 7.70-7.69 (d, 3H), 7.61-7.58 (m, 6H), 7.57-7.54 (m, 15H), 7.37-7.30 ppm (m, 15H): HRMS (FAB+): calcd for C57H39N6OP, 854.2923. found, (M+H) 855.3004.

Evaluation Example 2

Characteristics Evaluation of Compound 1

Evaluation of Thermal Characteristics of Compound 2

Figure 6:
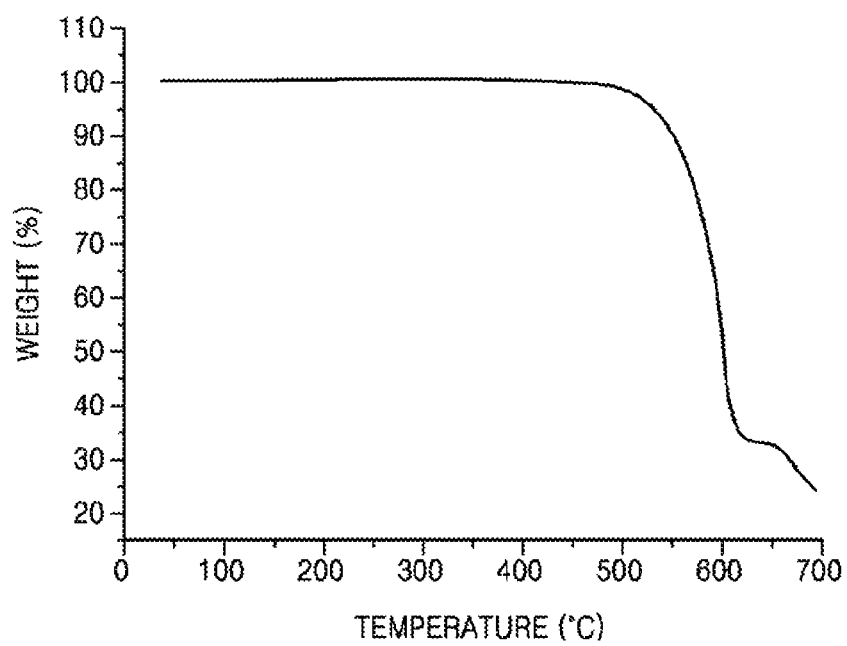
FIG. 6 is a graph showing TGA data of Compound 2 according to an embodiment of the present invention.
Figure 7:
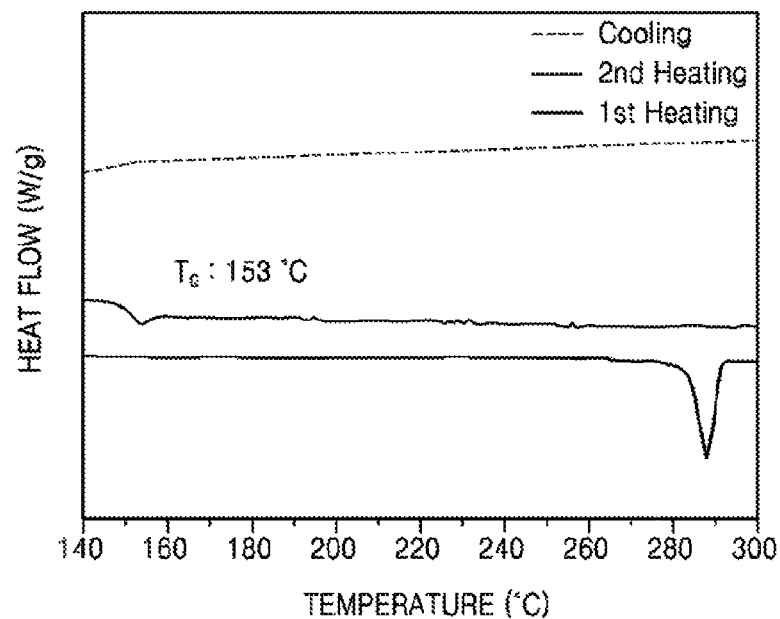
FIG. 7 is a graph showing DSC data of Compound 2 according to an embodiment of the present invention.

Thermal analysis was performed on Compound 2 in the same manner as in Evaluation Example 1. The results are shown in FIGS. 6 and 7. Referring to FIGS. 6 and 7, Compound 2 is found to have improved thermal stability.

Evaluation of Thermal Characteristics of Compound 2

Figure 8:
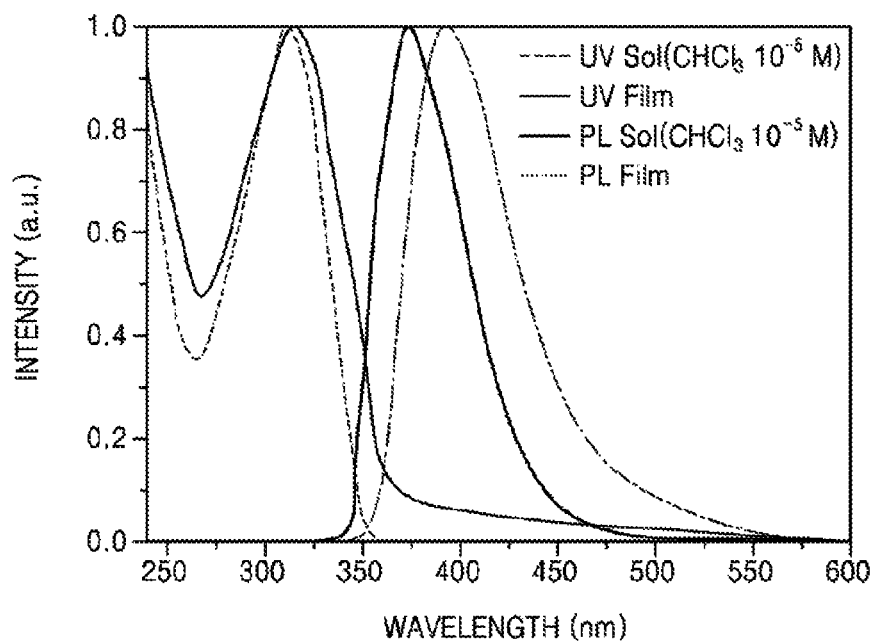
FIG. 8 is a graph showing spectroscopic analysis data of Compound 2 according to an embodiment of the present invention.

UV absorption and PL spectra of Compound 2 were evaluated in the same manner as described in Table 1 of Evaluation Example 1. The results are shown in FIG. 8. UV absorption peak wavelengths and PL peak wavelengths of Compound 2 are summarized in Table 4 below:

TABLE 4

| UV absorption peak wavelength$_{max}$ (nm) | | PL peak wavelength$_{max}$ (nm) | |
|---|---|---|---|
| UV_solution | UV_film | PL_solution | PL_film |
| 312 | 315 | 374 | 392 |

Referring to FIG. 8 and Table 4 above, Compound 2 is found to have appropriate spectroscopic characteristics for use as a material for organic light-emitting devices.

Evaluation of Electrochemical Characteristics of Compound 2

CV characteristics of Compound 2 were evaluated in the same manner as in Evaluation Example 1. The results are shown in FIG. 9.

Evaluation of HOMO and LUMO Energy Levels of Compound 2

Figure 9:
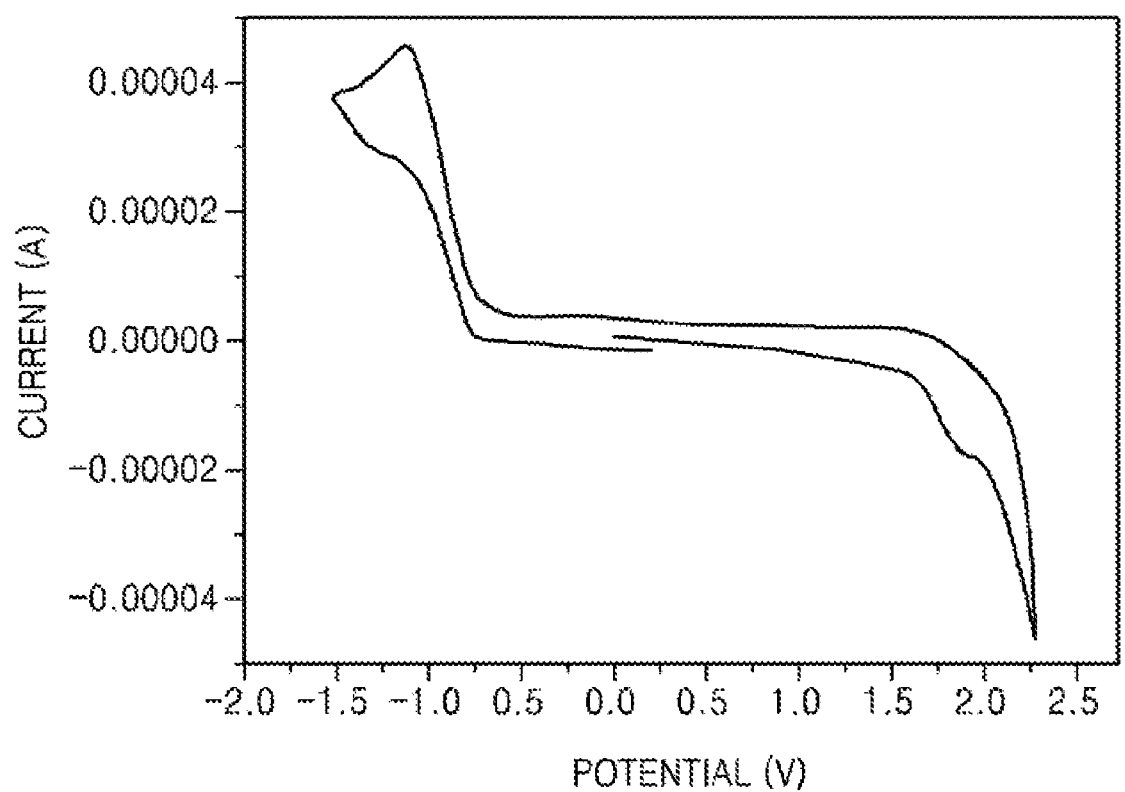
FIG. 9 is a graph showing cyclic voltametric analysis data of Compound 2 according to an embodiment of the present invention.

A LUMO energy level of Compound 2 was calculated using a reduction onset in FIG. 9. A HOMO energy level of Compound 2 was calculated using an optical band gap (Eg) based on the UV absorption edge in FIG. 8. The results are shown in Table 5.

TABLE 5

| HOMO(eV) | LUMO(eV) | Eg(eV) |
|---|---|---|
| −7.01 | −3.65 | 3.36 |

Example 1

An organic light-emitting device having a structure of "ITO/NPB (30 nm)/TCTA (10 nm)/CBP: 5 wt % Ir(ppy)$_3$ (30 nm)/Compound 1 (40 nm)/LiF (1 nm)/Al (110 nm)" was used as follows.

An ITO glass substrate (50×50 mm, 15Ω/□, available from SAMSUNG-Corning) for OLED was ultrasonically washed using distilled water and then isopropanol, followed by UV ozone cleaning for about 30 minutes. The washed glass substrate with transparent electrode lines attached was loaded onto a substrate holder, and NPB(N,N'-bis(naphthalen-1-yl)-N,N'-bis(phenyl)benzidine) was deposited on an ITO electrode (anode) to form a hole injection layer having a thickness of about 30 nm, followed by deposition of TCTA on the hole injection layer to form a hole transport layer having a thickness of about 10 nm. CBP (host) and Ir(ppy)$_3$ (tris(2-phenylpyridine)iridium(III)) (dopant, 5 wt %) were co-deposited on the hole transport layer to form an emission layer having a thickness of about 30 nm, followed by deposition of Compound 1 to form an electron transport layer having a thickness of about 40 nm. LiF was deposited on the electron transport layer to form an electron injecting layer having a thickness of about 1 nm, and Al was deposited on the electron injection layer to form a cathode having a thickness of about 110 nm, thereby completing the manufacture of the organic light-emitting device.

Comparative Example 1

An organic light-emitting device having a structure of "ITO/NPB (30 nm)/TCTA (10 nm)/CBP: 5 wt % Ir(ppy)$_3$(30 nm)/Compound E1 (40 nm)/LiF (1 nm)/Al (110 nm)" was manufactured in the same manner as in Example 1, except that Compound E1 below, instead of Compound 1, was used to form the electron transport layer.

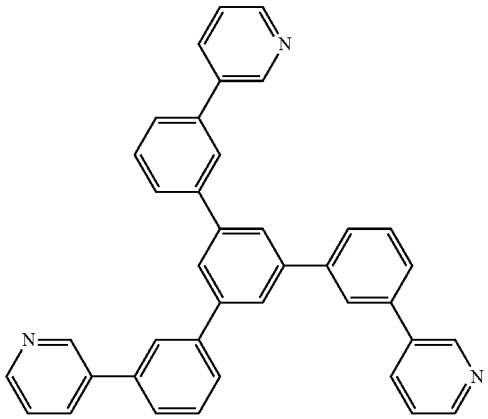

Compound E1

Example 2

An organic light-emitting device having a structure of "ITO/NPB (40 nm)/CBP: 5 wt % Ir(ppy)$_3$ (30 nm)/Compound 1 (10 nm)/Alq$_3$ (30 nm)/LiF (1 nm)/Al (110 nm)" was manufactured as follows.

An ITO glass substrate (50×50 mm, 15Ω/□, available from SAMSUNG-Corning) for OLED was ultrasonically washed using distilled water and then isopropanol, followed by UV ozone cleaning for about 30 minutes. The washed glass substrate with transparent electrode lines attached was loaded onto a substrate holder, and NPB (N,N'-bis(naphthalen-1-yl)-N,N'-bis(phenyl)benzidine) was deposited on an ITO electrode (anode) to form a hole injection layer having a thickness of about 40 nm, followed by co-deposition of CBP (host) and Ir(ppy)$_3$(tris(2-phenylpyridine)iridium(III)) (dopant, 5 wt %) on the hole injection layer to form an emission layer having a thickness of about 30 nm. Afterward, Compound 1 was deposited on the emission layer to form a hole blocking layer having a thickness of about 10 nm. After deposition of Alq$_3$ on the hole blocking layer to form an electron transport layer having a thickness of about 30 nm, LiF was deposited on the electron transport layer to form an electron injecting layer having a thickness of about 1 nm, followed by depositing Al on the electron injection layer to form a cathode having a thickness of about 110 nm, thereby completing the manufacture of the organic light-emitting device.

Comparative Example 2

An organic light-emitting device having a structure of "ITO/NPB (40 nm)/CBP: 5 wt % Ir(ppy)$_3$ (30 nm)/Alq$_3$ (40 nm)/LiF (1 nm)/Al (110 nm)" was manufactured in the same manner as in Example 3, except that the hole blocking layer including Compound 1 was not manufactured and the thickness of the electron transport layer was 40 nm.

Example 3

An organic light-emitting device having a structure of "ITO/NPB (40 nm)/TCTA (10 nm)/CBP: 5 wt % Ir(ppy)$_3$ (30 nm)/Compound 1 (10 nm)/Alq$_3$ (30 nm)/LiF (1 nm)/Al (110 nm)" was manufactured as follows.

An ITO glass substrate (50×50 mm, 15Ω/□, available from SAMSUNG-Corning) for OLED was ultrasonically washed using distilled water and then isopropanol, followed by UV ozone cleaning for about 30 minutes. The washed glass substrate with transparent electrode lines attached was loaded onto a substrate holder, and NPB(N,N'-bis(naphthalen-1-yl)-N,N'-bis(phenyl)benzidine) was deposited on an ITO electrode (anode) to form a hole injection layer having a thickness of about 40 nm, followed by depositing TCTA on the hole injection layer to form an electron blocking layer having a thickness of about 10 nm. CBP (host) and Ir(ppy)$_3$ (tris(2-phenylpyridine)iridium(III)) (dopant, 5 wt %) were co-deposited on the electron blocking layer to form an emission layer having a thickness of about 30 nm, followed by depositing Compound 1 to form a hole blocking layer having a thickness of about 10 nm. After deposition of Alq$_3$ on the hole blocking layer to form an electron transport layer having a thickness of about 30 nm, LiF was deposited on the electron transport layer to form an electron injecting layer having a thickness of about 1 nm, followed by depositing Al on the electron injection layer to form a cathode having a thickness of about 110 nm, thereby completing the manufacture of the organic light-emitting device.

Comparative Example 3

An organic light-emitting device having a structure of "ITO/NPB (40 nm)/TCTA (10 nm)/CBP: 5 wt % Ir(ppy)$_3$ (30 nm)/Alq$_3$ (40 nm)/LiF (1 nm)/Al (110 nm)" was manufactured in the same manner as in Example 3, except that the hole blocking layer including Compound 1 was not formed and the thickness of the electron transport layer was 40 nm.

Comparative Example 4

An organic light-emitting device was manufactured in the same manner as in Example 1, except that Compound A below was used as an electron transport layer forming material.

Compound A

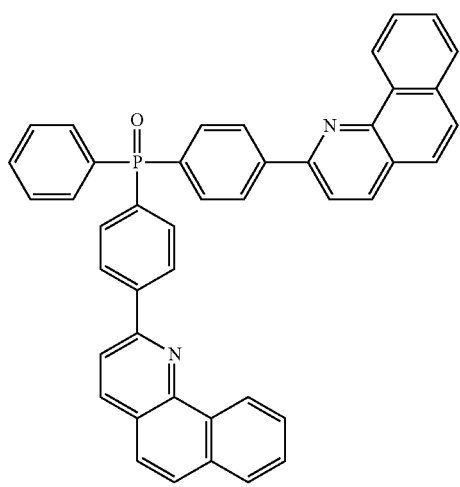

Comparative Example 5

An organic light-emitting device was manufactured in the same manner as in Example 1, except that Compound B below was used as an electron transport layer forming material.

Compound B

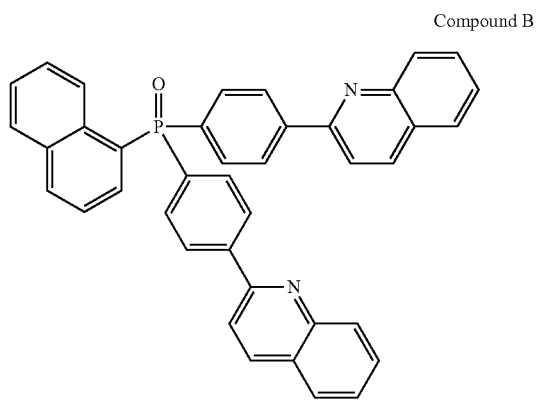 [SMILES: O=P(c1ccc(-c2ccc3ccccc3n2)cc1)(c1ccc(-c2ccc3ccccc3n2)cc1)c1cccc2ccccc12]

Comparative Example 6

An organic light-emitting device was manufactured in the same manner as in Example 1, except that Compound C below was used as an electron transport layer forming material.

Compound C

Evaluation Example 3

Characteristics Evaluation of Organic Light-emitting Devices

Driving voltages, luminances, external quantum efficiencies, efficiencies, power efficiencies, EL maximum peaks, and color purities of the organic light-emitting devices of Examples 1 to 3 and Comparative Examples 1 to 6 were evaluated using the following methods. The results are shown in Table 6 and Table 7.

Color coordinates were measured using a PR650 (Spectroscan) Source Measurement Unit. (available from Photo Research, Inc.) with a supply of power using a Kethley Source-Measure Unit (SMU 236).

Luminances were measured using a PR650 (Spectroscan) Source Measurement Unit. (available from Photo Research, Inc.) with a supply of power using a Kethley Source-Measure Unit (SMU 236).

Efficiencies were measured using a PR650 (Spectroscan) Source Measurement Unit. (available from Photo Research, Inc.) with a supply of power using a Kethley Source-Measure Unit (SMU 236).

TABLE 6

| | Driving voltage (V) (at 1 cd/m²) | Luminance (cd/m²) (Vmax) | External quantum efficiency (%) (V) |
|---|---|---|---|
| Comparative Example 1 | 3.5 | 33490 (13)[1] | 17.03 (5.5) |
| Example 1 | 4 | 72080 (14.5) | 22.19 (9) |
| Comparative Example 2 | 4 | 33040 (12.5) | 3.85 (8) |
| Example 2 | 5 | 61030 (13) | 11.45 (10.5) |
| Comparative Example 3 | 3.5 | 35770 (13) | 5.45 (9) |
| Example 3 | 4.5 | 71150 (12.5) | 14.62 (9.5) |
| Comparative Example 4 | 5.5 | 38050 (14) | 7.55 (11) |
| Comparative Example 5 | 5.3 | 39550 (14) | 8.43 (10.8) |
| Comparative Example 6 | 5 | 46520 (13.5) | 8.94 (10) |

TABLE 7

| | Efficiency (cd/A) (at 1 cd/m²) | Power efficiency (Lm/W) (V) | EL peak wavelength (nm) |
|---|---|---|---|
| Comparative Example 1 | 52.02 (5.5) | 32.81 (4.5) | 512 |
| Example 1 | 68.37 (9) | 24.44 (8.5) | 512 |
| Comparative Example 2 | 11.63 (8) | 5.10 (6.5) | 512 |
| Example 2 | 35.39 (10.5) | 10.75 (10) | 512 |
| Comparative Example 3 | 44.98 (9.5) | 14.87 (9.5) | 512 |
| Example 3 | 69.98 (9.5) | 25.87 (9.5) | 512 |
| Comparative Example 4 | 38.25 (10.9) | 8.33 (10.2) | 512 |
| Comparative Example 5 | 40.89 (11.5) | 8.96 (10.5) | 512 |
| Comparative Example 6 | 41.55 (11.9) | 9.25 (11) | 512 |

[1]: a voltage in volts (V) at which luminance, external quantum efficiency, efficiency, and power were measured.

Referring to Tables 6 and 7, the organic light-emitting devices of Examples 1 to 3 are found to have improved characteristics as compared with the organic light-emitting devices of Comparative Examples 1 to 6.

As described above, according to the one or more embodiments of the present invention, a phosphine oxide-based compound of Formula 1 above may have improved thermal stability and optical characteristics, and a low HOMO energy level (i.e., with a large absolute of the HOMO energy level). Therefore, an organic light-emitting device using the phosphine oxide-based compound of Formula 1 may have a low driving voltage, a high efficiency, and a high color purity.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A phosphine oxide-based compound represented by Formula 1 below:

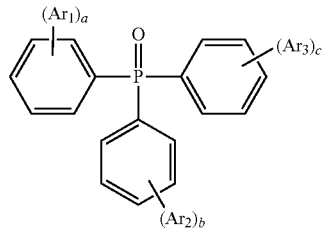

Formula 1 wherein $Ar_1$ to $Ar_3$ are each independently deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or an N-containing electron withdrawing group;

a, b and c are each independently an integer from 0 to 5;

the sum of a, b, and c must be greater than or equal to 1; and at least one of a number of $Ar_1$s, b number of $Ar_2$s, and c number of $Ar_3$s is an N-containing electron withdrawing group, wherein the N-containing electron withdrawing group is selected from among:

a substituted or unsubstituted pyrrolyl group,
a substituted or unsubstituted pyrazolyl group,
an unsubstituted imidazolyl group,
a substituted or unsubstituted imidazolinyl group,
a substituted or unsubstituted imidazopyridinyl group,
a substituted or unsubstituted imidazopyrimidinyl group,
a substituted or unsubstituted pyrazinyl group,
an unsubstituted pyrimidinyl group,
a substituted benzoimidazolyl group,
a substituted or unsubstituted indolyl group,
a substituted or unsubstituted purinyl group,
a substituted or unsubstituted quinolinyl group,
a substituted or unsubstituted isoquinolyl group,
a substituted or unsubstituted phthalazinyl group,
a substituted or unsubstituted indolizinyl group,
a substituted or unsubstituted naphthyridinyl group,
a substituted or unsubstituted quinazolinyl group,
a substituted or unsubstituted cinnolinyl group,
a substituted or unsubstituted indazolyl group,
a substituted or unsubstituted isothiazolyl group,
a substituted or unsubstituted isoxazolyl group,
a substituted or unsubstituted triazinyl group,
a substituted or unsubstituted oxadiazolyl group,
a substituted or unsubstituted pyridazinyl group,
a substituted or unsubstituted triazolyl group,
a substituted or unsubstituted tetrazolyl group,
a substituted or unsubstituted benzothiazolyl group, and
a substituted or unsubstituted benzoxazolyl group.

2. The phosphine oxide-based compound of claim 1, wherein the N-containing electron withdrawing group is selected from among:
an unsubstituted pyrimidinyl group,
a substituted or unsubstituted pyrazinyl group,
a substituted or unsubstituted triazinyl group,
a substituted or unsubstituted quinolinyl group,
a substituted or unsubstituted isoquinolinyl group,
a substituted benzoimidazolyl group,
a substituted or unsubstituted imidazopyridinyl group,
a substituted or unsubstituted imidazopyrimidinyl group,
a substituted or unsubstituted benzothiazolyl group, and
a substituted or unsubstituted benzoxazolyl group.

3. The phosphine oxide-based compound of claim 1, wherein the N-containing electron withdrawing group is represented by one of Formulae 2C to 2L:

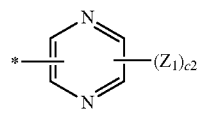
Formula 2C

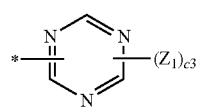
Formula 2D

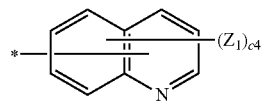
Formula 2E

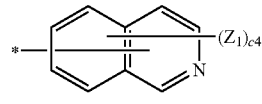
Formula 2F

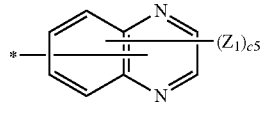
Formula 2G

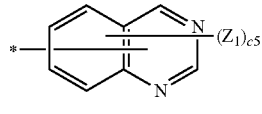
Formula 2H

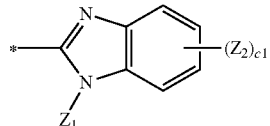
Formula 2I

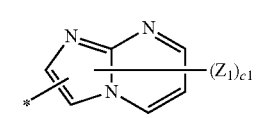
Formula 2J

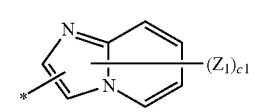
Formula 2K

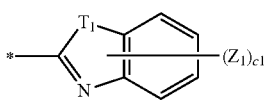
Formula 2L wherein $Z_1$ and $Z_2$ are each independently selected from deuterium, a halogen atom, a hydroxyl group, a cyano group, a nitro group, an amino group, an amidino group, hydrazine, hydrazone, a carboxyl group and a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group and a $C_6$-$C_{60}$ aryl group; a $C_6$-$C_{60}$ aryl group substituted with at least one of —F, —CN, and a $C_1$-$C_{10}$ alkyl group; and a $C_6$-$C_{60}$ aryloxy group, a $C_6$-$C_{60}$ arylthio group and a $C_2$-$C_{60}$ heteroaryl group;

$c_1$ is an integer from 0 to 4;
$c_2$ is an integer of 0 to 3;
$c_3$ is an integer from 0 to 2;
$c_4$ is an integer of 0 to 6;
$c_5$ is an integer from 0 to 5; and
$T_1$ is O or S.

4. The phosphine oxide-based compound of claim 3, wherein the $Z_1$ and $Z_2$ are each independently deuterium, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, or a phenanthrenyl group.

5. The phosphine oxide-based compound of claim 2, wherein the N-containing electron withdrawing group is represented by Formula 2I below:

Formula 2I

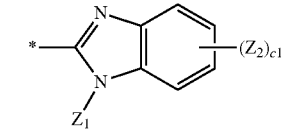

wherein $Z_1$ is a phenyl group, a naphthyl group, an anthryl group, or a phenanthrenyl group, and $Z_2$ is independently selected from deuterium, a halogen atom, a hydroxyl group, a cyano group, a nitro group, an amino group, an amidino group, hydrazine, hydrazone, a carboxyl group and a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group and a $C_6$-$C_{60}$ aryl group; a $C_6$-$C_{60}$ aryl group substituted with at least one of —F, —CN, and a $C_1$-$C_{10}$ alkyl group; and a $C_6$-$C_{60}$ aryloxy group, a $C_6$-$C_{60}$ arylthio group and a $C_2$-$C_{60}$ heteroaryl group; and
$c_1$ is an integer from 0 to 4.

6. The phosphine oxide-based compound of claim 1, wherein at least two of the a number of $Ar_1$s, the b number of $Ar_2$s, and the c number of $Ar_3$s are N-containing electron withdrawing groups.

7. The phosphine oxide-based compound of claim 1, wherein a, b, and c are all 1, and at least two of $Ar_1$, $Ar_2$, and $Ar_3$ are N-containing electron withdrawing groups.

8. The phosphine oxide-based compound of claim 1, wherein the phosphine oxide-based compound is a compound represented by Formula 1A below:

Formula 1A

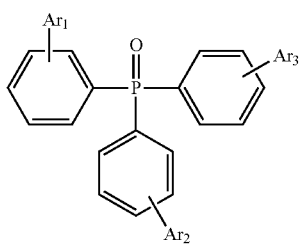

wherein $Ar_1$ to $Ar_3$ are each independently deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or an N-containing electron withdrawing group; and at least one of $Ar_1$, $Ar_2$, and $Ar_3$ is an N-containing electron withdrawing group, wherein the N-containing electron withdrawing group is selected from among one of Formulae 2C to 2L:

Formula 2C

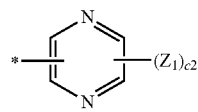

Formula 2D

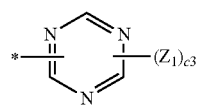

Formula 2E

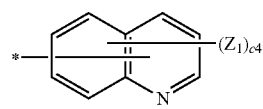

Formula 2F

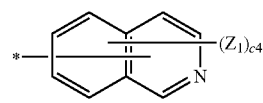

Formula 2G

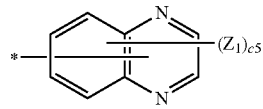

Formula 2H

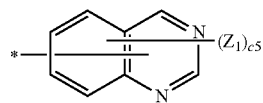

Formula 2I

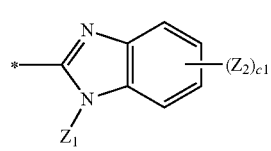

Formula 2J

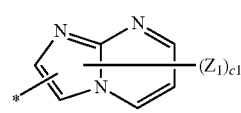

Formula 2K

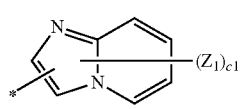

Formula 2L

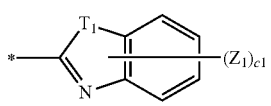

wherein $Z_1$ and $Z_2$ are each independently selected from deuterium, a halogen atom, a hydroxyl group, a cyano group, a nitro group, an amino group, an amidino group, hydrazine, hydrazone, a carboxyl group and a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group and a $C_6$-$C_{60}$ aryl group; a $C_6$-$C_{60}$ aryl group substituted with at least one of —F, —CN, and a $C_1$-$C_{10}$ alkyl group; and a $C_6$-$C_{60}$ aryloxy group, a $C_6$-$C_{60}$ arylthio group and a $C_2$-$C_{60}$ heteroaryl group;

$c_1$ is an integer from 0 to 4;

$c_2$ is an integer of 0 to 3;

$c_3$ is an integer from 0 to 2;

$c_4$ is an integer of 0 to 6;

$c_5$ is an integer from 0 to 5; and $T_1$ is O or S.

9. The phosphine oxide-based compound of claim 8, wherein $Z_1$ and $Z_2$ are each independently deuterium, a halogen atom, a hydroxyl group, a cyano group, a nitro group, an amino group, an amidino group, hydrazine, hydrazone, a carboxyl group and a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, or a phenanthrenyl group.

10. The phosphine oxide-based compound of claim 8, wherein at least two of $Ar_1$, $Ar_2$, and $Ar_3$ are N-containing electron withdrawing groups.

11. The phosphine oxide-based compound of claim 8, wherein the phosphine oxide-based compound is a compound represented by Formula 1A-(1):

Formula 1A-(1)

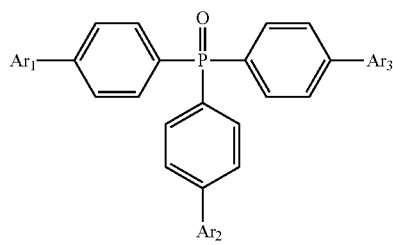

wherein $Ar_1$, $Ar_2$, and $Ar_3$ are each independently selected from among deuterium, a halogen atom, a hydroxyl group, a cyano group, a nitro group, an amino group, an amidino group, hydrazine, hydrazone, a carboxyl group and a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a phenanthrenyl group, and groups represented by Formulae 2A to 2M, wherein at least one of $Ar_2$, $Ar_2$, and $Ar_3$ is selected from among groups represented by Formulae 2C to 2M:

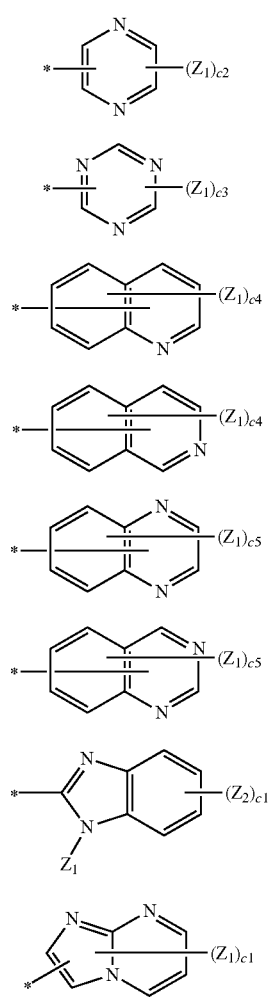

Formula 2C

Formula 2D

Formula 2E

Formula 2F

Formula 2G

Formula 2H

Formula 2I

Formula 2J

Formula 2K

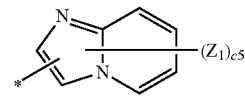

Formula 2L

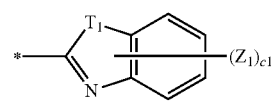

Formula 2M

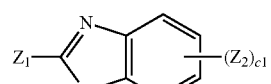

wherein $Z_1$ and $Z_2$ are each independently deuterium, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, or a phenanthrenyl group;

$c_1$ is an integer from 0 to 4;
$c_2$ is an integer of 0 to 3;
$c_3$ is an integer from 0 to 2;
$c_4$ is an integer of 0 to 6;
$c_5$ is an integer from 0 to 5; and
$T_1$ is O or S.

12. The phosphine oxide-based compound of claim 1, wherein the phosphine oxide-based compound is one of Compounds 1 to 6 below:

Compound 1

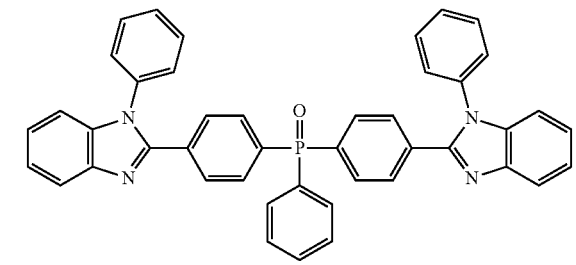

Compound 2

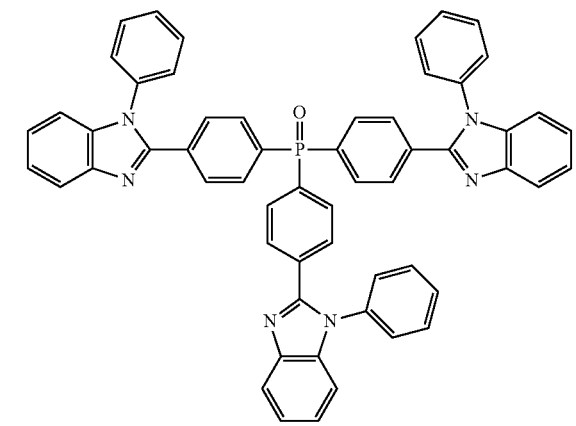

-continued

Compound 3

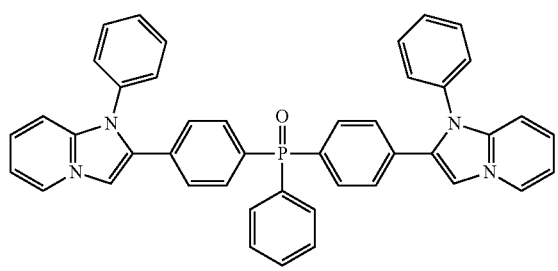

Compound 4

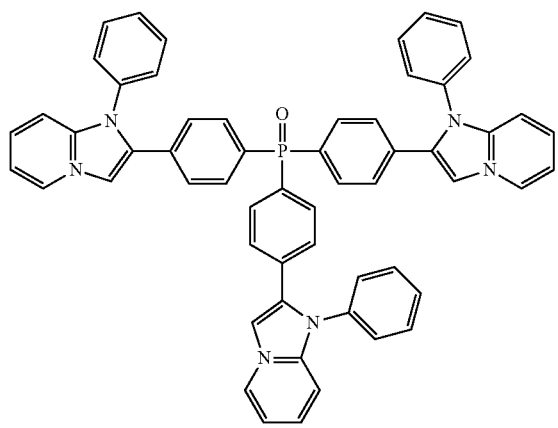

Compound 5

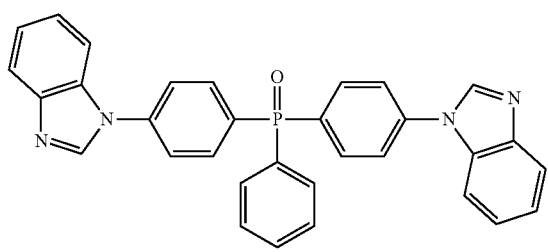

-continued

Compound 6

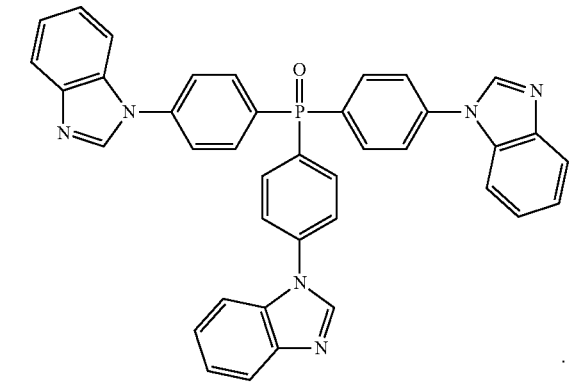

13. The phosphine oxide-based compound of claim 1, wherein the phosphine oxide-based compound has a highest occupied molecular orbital (HOMO) energy level of about −7.0 eV or less.

14. An organic light-emitting device comprising:
a first electrode;
a second electrode disposed opposite to the first electrode; and
an organic layer disposed between the first electrode and the second electrode and comprising an emission layer, wherein the organic layer comprises at least one of the phosphine oxide-based compounds of claim 1.

15. The organic light-emitting device of claim 14, wherein the organic layer further comprises at least one of a hole injection layer, a hole transport layer, a functional layer having both hole injection and hole transport capabilities, a buffer layer, and an electron blocking layer between the first electrode and the emission layer.

16. The organic light-emitting device of claim 14, wherein the organic layer further comprises at least one of a hole blocking layer, an electron transport layer, a functional layer having both electron injection and electron transport capabilities and an electron injection layer between the emission layer and the second electrode.

17. The organic light-emitting device of claim 16, wherein the organic layer further comprises an electron transport layer between the emission layer and the second electrode, and the electron transport layer comprises at least one of the phosphine oxide-based compounds.

18. The organic light-emitting device of claim 17, wherein the electron transport layer further comprises a lithium (Li) complex.

19. The organic light-emitting device of claim 16, wherein the organic layer further comprises a hole blocking layer and an electron transport layer between the emission layer and the second electrode, and the hole blocking layer comprises at least one of the phosphine oxide-based compounds.

20. The organic light-emitting device of claim 14, wherein the emission layer comprises a host and a dopant, and the dopant is a phosphorescent dopant emitting light based on the mechanism of phosphorescence.

* * * * *